(12) United States Patent
Tobola et al.

(10) Patent No.: US 8,398,557 B2
(45) Date of Patent: Mar. 19, 2013

(54) SPREAD-SPECTRUM METHOD FOR DETERMINING PHYSIOLOGICAL PARAMETERS

(75) Inventors: Andreas Tobola, Erlangen (DE); Ulrich Vogl, Ebermannsdorf (DE); Hans-Joachim Moersdorf, Fuerth (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 515 days.

(21) Appl. No.: 12/280,156

(22) PCT Filed: Feb. 6, 2007

(86) PCT No.: PCT/EP2007/001002
§ 371 (c)(1),
(2), (4) Date: Aug. 3, 2010

(87) PCT Pub. No.: WO2007/104390
PCT Pub. Date: Sep. 20, 2007

(65) Prior Publication Data
US 2010/0292593 A1    Nov. 18, 2010

(30) Foreign Application Priority Data
Feb. 20, 2006  (DE) .......................... 10 2006 007 879
May 11, 2006  (DE) .......................... 10 2006 022 120

(51) Int. Cl.
*A61B 5/02* (2006.01)
(52) U.S. Cl. ...................................................... 600/508
(58) Field of Classification Search .................. 600/476, 600/508
See application file for complete search history.

(56) References Cited

U.S. PATENT DOCUMENTS

| | | | |
|---|---|---|---|
| 5,503,148 A | 4/1996 | Pologe | |
| 5,560,367 A | 10/1996 | Haardt et al. | |
| 5,630,413 A | 5/1997 | Thomas et al. | |
| 5,835,712 A | 11/1998 | Dufresne | |
| 5,921,921 A | 7/1999 | Potratz et al. | |
| 6,002,952 A | 12/1999 | Diab et al. | |
| 6,334,065 B1 | 12/2001 | Al-Ali et al. | |
| 6,411,833 B1 | 6/2002 | Baker et al. | |
| 6,587,701 B1 * | 7/2003 | Stranc et al. | 600/310 |
| 6,714,803 B1 | 3/2004 | Mortz | |
| 2002/0012008 A1 | 1/2002 | Takagi | |
| 2002/0136264 A1 * | 9/2002 | Herleikson et al. | 375/130 |
| 2004/0030229 A1 | 2/2004 | Norris | |
| 2004/0204638 A1 * | 10/2004 | Diab et al. | 600/336 |
| 2004/0225225 A1 | 11/2004 | Naumov et al. | |
| 2005/0187451 A1 * | 8/2005 | Norris | 600/326 |
| 2007/0255779 A1 | 11/2007 | Watts, III | |

FOREIGN PATENT DOCUMENTS
CA        2357059      5/1996
DE     69229994 T2    4/2000
(Continued)

*Primary Examiner* — Tse Chen
*Assistant Examiner* — Hien Nguyen
(74) *Attorney, Agent, or Firm* — Michael A. Glenn; Glenn Patent Group

(57) ABSTRACT

An apparatus including a receiver and an extractor is provided for determining a physiological parameter of a living being. The receiver is adapted to receive iterating optical signals, the optical signal including sequences, and a sequence including at least two bright periods during which a transmit light source adopts an on state and at least one dark period during which no transmit light source adopts an on state, and the at least two bright periods being irregularly arranged within a sequence. In addition, the apparatus includes an extractor. The extractor extracts information on the physiological parameter from a receive signal, the extractor being adapted to extract, on the basis of the information on the arrangement of the bright periods within the sequence, a value of a magnitude indicating a vital parameter.

26 Claims, 22 Drawing Sheets

FOREIGN PATENT DOCUMENTS

| | | |
|---|---|---|
| EP | 208201 | 1/1987 |
| EP | 314331 | 5/1989 |
| EP | 341059 | 11/1989 |
| EP | 0502717 | 9/1992 |
| EP | 1254628 | 11/2002 |
| EP | 1357481 A2 | 10/2003 |
| EP | 1374764 | 1/2004 |
| WO | WO 98/17172 | 4/1998 |
| WO | WO-02054950 | 7/2002 |

* cited by examiner

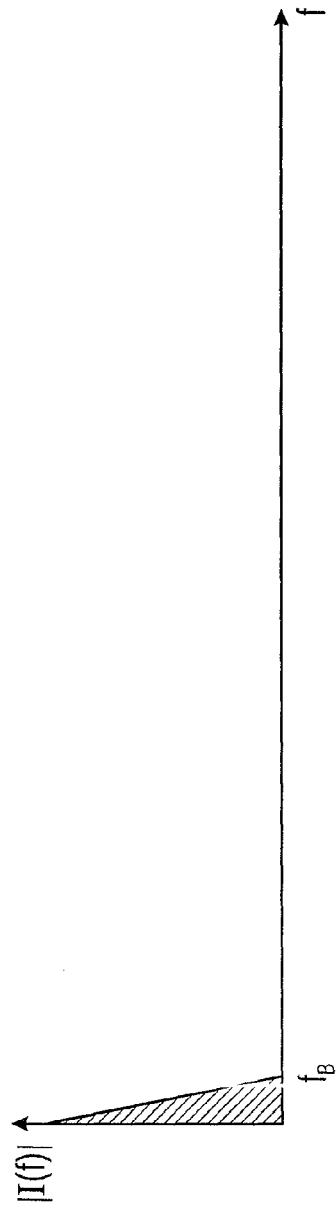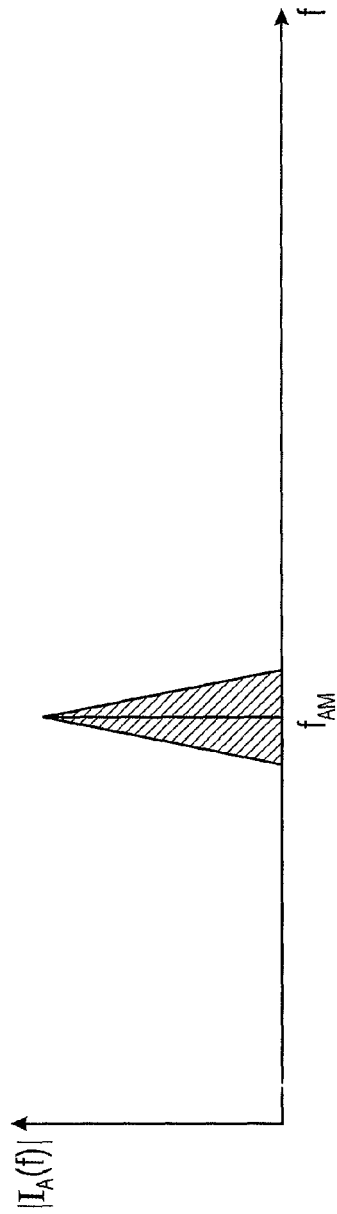
FIG 4
FIG 5

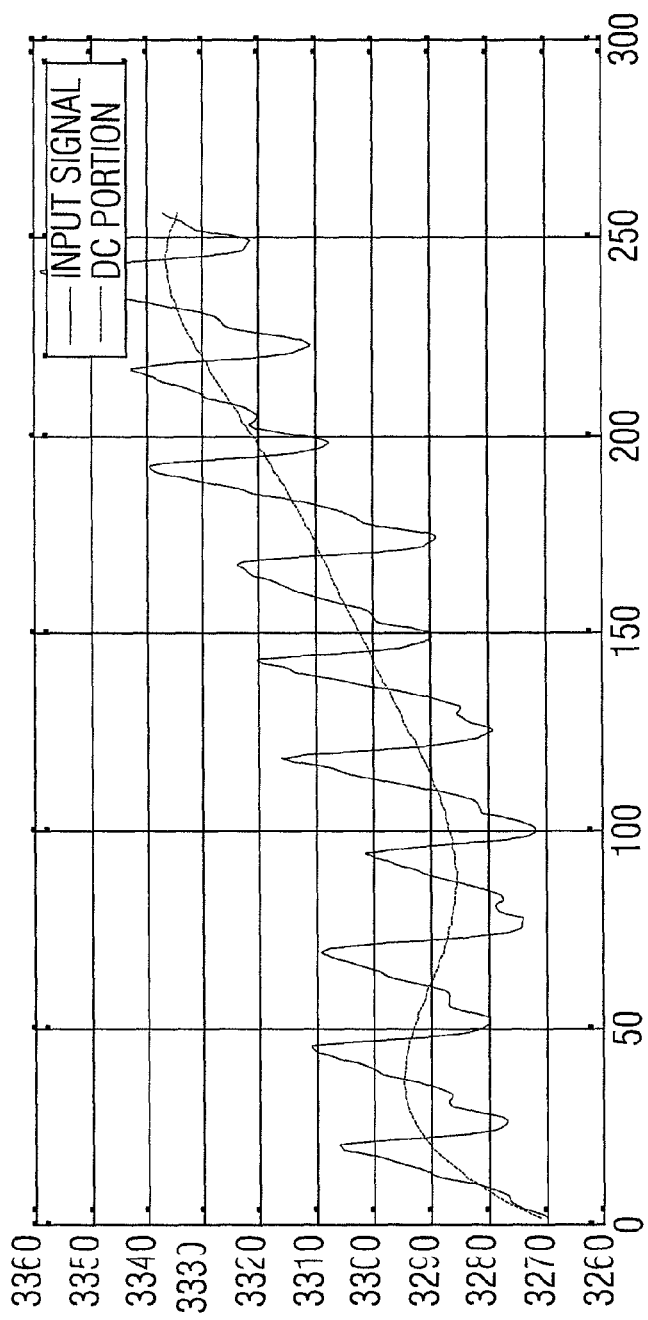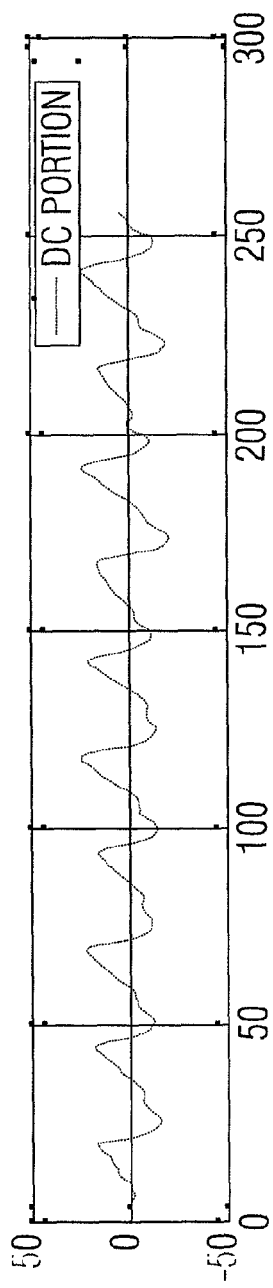
FIG 15A
FIG 15B

SPREAD-SPECTRUM METHOD FOR DETERMINING PHYSIOLOGICAL PARAMETERS

BACKGROUND OF THE INVENTION

The present invention relates to an apparatus for determining a physiological parameter of a living being. The method may be applied in plethysmogram-based measuring methods (e.g. plethysmography, pulse oximetry) for the purpose of reduced susceptibility to ambient-light interferences and electromagnetic interferences.

Plethysmography is an optical method of obtaining a so-called plethysmogram which provides information about the pulse frequency and the oxygen saturation of the blood of a subject. A plethysmogram is a graphic illustration of volume changes. In this field of application, it is specifically the volume changes of an arterial blood flow at a localized measurement site of the human body which are detected as the plethysmogram. To implement this in technical terms, light is radiated through tissue at a body location having arterial blood vessels. The patient has a sensor applied to him/her which contains a light source and a photoreceiver, so that the light passes through the tissue layer, and so that the remaining light intensity impinges upon the photoreceiver. Within the body, the light undergoes an attenuation which is dependent, among other things, on the wavelength of the light source, the type and concentration of the substances in the irradiated tissue, and on the pulsation of the blood. The signal of the photoreceiver which has thus been obtained is present in the form of a photocurrent, is dependent on the above-mentioned general conditions, and corresponds, in a first approximation, to the changes in the blood volume of arterial vessels which are caused by contraction of the heart muscle. FIG. 24 shows the basic architecture of an apparatus for detecting a plethysmogram. A microcontroller (μC) controls, via two driver stages, two LEDs of different wavelengths, one light source being sufficient, in principle, for creating a plethysmogram. The LEDs depicted in FIG. 24 emit light in the red and infrared regions. The light emitted by the LEDs subsequently passes through the tissue of the subject, in FIG. 24 this is depicted, by way of example, as a finger. Once the light has passed through the tissue of the subject, it will impinge upon a photosensor. The photsensor converts the optical signals into electrical signals and passes them on to processing electronics which amplify the signal, convert them from analog to digital and feed them to the microcontroller (μC). The microcontroller (μC) then determines two plethysmograms, one plethysmogram for each wavelength, from the digital signals fed to it. From the waveforms of the plethysmograms thus measured, physiological parameters, such as the heart rate or the oxygen saturation of the subject's blood, may be measured, with one single plethysmogram being sufficient, in principle, for determining the heart rate, for determining the oxygen saturation of the blood, two plethysmograms of light sources of different wavelengths being useful.

Pulse oximetry is a non-invasive method of measuring the oxygen saturation of the blood ($SpO_2$) and the heart rate (HR) by means of an optical sensor. The oxygen saturation detected by the pulse oximeter is specifically referred to as the $SpO_2$ value. The oxygen saturation is defined as the ratio of the concentration of oxygen-saturated hemoglobin molecules and the overall hemoglobin concentration, and is indicated in percent. A component of the pulse oximeter is a sensor having two integrated light sources and being configured similar to a plethysmograph, cf. FIG. 24. In pulse oximetry, use is made of at least two plethysmograms to determine the color of the arterial blood. The color of the blood, in turn, is dependent on the oxygen saturation. By selecting the wavelengths of the light sources well, it may be shown that a quantity correlating well with the oxygen saturation may be obtained from the ratios of prominent points within the plethysmogram. Typically, the spectra of the receive signals of two light sources of different wavelengths are determined, and the quotient of specific spectral values is formed. This quotient will then be approximately proportional to the $SpO_2$ value of the blood.

An essential quality characteristic in comparing pulse oximeters is the resistance toward interferences. Filtering those unuseful signal portions which arise because of the movement of the patient is particularly problematic. Even with small movements, the amplitudes of the motion artifacts may seem larger than those of the pulse wave within the signal. If the signal is highly overlaid by motion artifacts, this will lead to a temporary operational failure of the equipment, with this problem being signaled accordingly. In the worst case, the equipment will not detect the distorted measurement and will not issue a signal, so that the measurement values indicated will erroneously be held as true. The quality of treatment of a patient may be clearly reduced due to measurement values being incorrectly indicated. Especially in the environment of operating rooms, the above-mentioned distortions represent a major disadvantage of pulse oximeters.

In addition to the motion artifacts, high-power light sources, such as those of operating-room lamps, fluorescent lamps or monitors, may cause unwanted interferences in the signal. With conventional pulse oximeters or plethysmographs, this problem is typically diminished by introducing additional measurement periods for determining the ambient light, and by subsequently subtracting the ambient-light measurement from the useful-signal measurement. During these measurement periods or time slots, all light sources of the sensor are switched off, and only the ambient light is measured. The ambient-light intensity is subtracted from the plethysmogram, and thus the portion of ambient light is largely separated from the pulse signal. However, especially with pulsating or AC-powered ambient-light sources, an interference portion will remain within the plethysmogram. The interference portion within the plethysmogram thus highly depends on the electronic equipment, or interferers, used in the surroundings. Especially in the intensive care of patients, a multitude of electronic devices and tools are employed, so that the susceptibility of pulse oximeters and plethysmographs to interference is a given fact particularly in intensive-care environments. Particularly in the field of intensive care, however, measurement errors of physiological parameters such as the heart rate or the blood oxygen saturation are extremely critical and may entail serious consequences.

In pulse oximetry, transmission and remission sensors have several LEDs (transmitters) and only one photodiode (receiver). The subject's tissue is irradiated by LEDs of different wavelengths, and the photodiode receives the light of different wavelengths from the tissue. In principle, it would be possible to differentiate various channels by means of the wavelengths of the LEDs, e.g. by color filters present at several photodiodes. Since this involves a large amount of technical expenditure on the side of the photodiode, the intensities of the LEDs may be modulated. Only then is it possible to differentiate between the wavelengths by means of a single broad-band photodiode.

In order to enable the receiver to differentiate between various transmit sources (LEDs) having different wavelengths, TDMA concepts (time division multiple access) are employed with known pulse oximeters. Each sensor LED has a time window assigned to it within which it is switched on. FIG. 25 illustrates this time sequence of signals. One may recognize that the various LEDs successively have time slots of equal durations associated with them which are separated by dark periods of equal durations. FIG. 25 shows a schematic sequence with three different LEDs. The LEDs of different wavelengths successively light up for a short time duration, in FIG. 25, the bright periods of the LEDs are designated by "LED 1", "LED 2", and "LED 3". Typical frequencies with which the light sources of current pulse oximeters are controlled amount to 20-50 Hz. By adding additional dark phases during which none of the LEDs lights up, designated by "DARK" in FIG. 25, one tries to measure the signal portion caused by ambient light, and to subsequently subtract it from the useful signal. Nevertheless, the results are often distorted by ambient light or by high-frequency surgery influences. In high-frequency surgery, tissue is cut by means of high-frequency voltages. These high frequencies cause inductions in lines of the pulse oximeters and may thus interfere with their functioning. The local influences may be largely suppressed, since the sensors are protected against irradiation from the outside. Nevertheless, ambient light will enter into the shell of the sensor. The signal quality is clearly improved by subtracting the ambient-light portion, determined by adding dark phases. However, interference artifacts will remain which may lead to incorrect $SpO_2$ values. Up to now, it has not been possible, despite numerous attempts, to remove those interferences, which are caused by fluorescent lamps, infrared heat lamps, operating-room illumination and monitors, from the useful signal.

A further example of dynamic interferences may be found with subjects who have long-term measurements conducted on them. They wear a sensor with integrated LEDs and a photoreceiver over a relatively long time period for detecting long-term data. These patients or subjects, for example during car journeys through tree-lined streets or streets lined by many high buildings, are subject to pronounced and, as the case may be, rapid changes in the lighting conditions. In places, these changing lighting conditions express themselves in a manner very similar to the interferences in in-patient environments of hospitals. In principle, subjects subjected to long-term measurements are exposed to a multiplicity of ambient-light influences which may give rise to a whole spectrum of interferences.

The susceptibility of current pulse oximeters and plethysmographs to interferences will rise if the above-mentioned interferers are located within their surroundings. Especially in operating rooms or intensive-care units, there are a multiplicity of electronic devices, or electronic interferers. Particularly in such environments, thus, the susceptibility of current pulse oximeters and plethysmographs to interferences increases. This significant disadvantage may entail serious consequences for subjects if such situations give rise to measurement errors which cannot be immediately identified as such.

Known plethysmography methods may be found in the following documents, for example:

EP 1374764 A1/WO 2002054950 A08, which describes a basic circuit for measuring and detecting a plethysmogram, and deals with the above-described signal processing in detail.

EP 208201 A2/A3, wherein optical detection of a change of volume of a body part, and an evaluation device for evaluating the optical signals are protected, in principle. The method described there makes use of the changing outward volume change of extremities caused by the pulse and the changes in blood pressure associated therewith.

EP 341059 A3. Here, a basic pulse oximetry method is described which exploits light sources (LEDs) of different wavelengths. Light of different wavelengths is radiated through the subject's tissue, the light signals are absorbed from the tissue by means of optical sensors and are evaluated by a corresponding analog signal processing.

EP 314331 B1, a pulse oximetry method also based on light of different wavelengths is used for radiating the tissue of a subject. The optical signals thus obtained are converted to electric signals, and a value which provides insights into the oxygen saturation of the subject's blood is extracted therefrom.

EP 1254628 A1, the pulse oximeter protected here is also configured to determine oxygen saturation of blood, the method proposed here additionally reducing interferences caused by cross-talk.

U.S. Pat. Nos. 5,503,148/6,714,803, here a description is given of signal processing methods for linear regression which determine an $SpO_2$ value by means of two plethysmograms. A correlation coefficient which serves as the reliability measure is determined from among the two plethysmograms.

DE 692 29 994 T2 discloses a signal processor taking up a first signal and a second signal correlated with the first signal. Both signals each have a useful signal portion and an unuseful signal portion. The signals may be taken up by the spreading of energy through a medium and by measuring an attenuated signal after transmission or reflection. Alternatively, the signals may be taken up by measuring energy created by the medium.

The first and second signals measured are processed so as to take up a noise reference signal which does not include the useful signal portions of the respective first and second signals measured. The remaining unuseful signal portions of the first and second signals measured are combined to shape a noise reference signal. This noise reference signal is correlated with each of the unuseful signal portions of the first and second signals measured.

The noise signal is then used to remove the unuseful signal portions within the first. and second signals measured by means of an adaptive noise eliminating means. An adaptive noise eliminating means may be seen analogously to a dynamic multiband-stop filter which dynamically changes its transfer function in response to a noise reference signal and to the signal measured so as to eliminate frequencies from the signals measured which are also present in the noise reference signal. A typical adaptive noise eliminating means thus obtains the signal from which noise is to be eliminated, and a noise reference signal. The output of the adaptive noise eliminating means then is the useful signal with reduced noise.

US 2005/0187451 describes a method of use in a signal attenuation measurement for determining a physiological parameter of a patient. Further, a description is given of an apparatus for determining a physiological parameter of a patient from at least two signals which passed tissue of the patient and were attenuated there. In this context, the two signals are multiplexed using an FOCDM method (FOCDM=frequency orthogonal code division multiplex). The method enables separation of the two signals and suppression of external interference.

SUMMARY

According to an embodiment, an apparatus for determining a physiological parameter of a living being may have: a receiver adapted to receive iterating optical signals, an optical signal including sequences, and a sequence including at least two bright periods during which a transmit light source adopts an on state and at least two dark periods during which no transmit light source adopts an on state, and the at least two bright periods being irregularly arranged within a sequence, and an extractor for extracting information on the physiological parameter from the receive signal, the extractor being adapted to receive, to store or to generate binary code words including a length and indicating an arrangement of the bright and dark periods, and to link a binary code word with the signals in a block-by-block manner so as to obtain a digital signal of a bright transmit channel, the bright transmit channel being determined by the binary code word, and to link two other binary code words with the signals so as to obtain two digital signals of two dark transmit channels which are determined by the two other binary code words, and the extractor being adapted to extract, on the basis of the digital signal of the bright transmit channel and of the two digital signals of the dark transmit channels, a value of a magnitude indicating the physiological parameter, the extractor being implemented to form a differential signal from the two dark transmit channels, and to reduce an aliasing interference in the digital signal of the bright transmit channel by means of a spectral analysis of the differential signal.

According to another embodiment, a method of determining a physiological parameter of a living being may have the steps of: receiving iterating optical signals, an optical signal including sequences, and a sequence including at least two bright periods during which a transmit light source adopts an on state and at least two dark periods during which no transmit light source adopts an on state, and the at least two bright periods being irregularly arranged within a sequence, and extracting information on the physiological parameter from the receive signal, binary code words which include a length and indicate an arrangement of the bright and dark periods being received, stored or generated; linking a binary code word with the signals in a block-by-block manner so as to obtain a digital signal of a bright transmit channel, the bright transmit channel being determined by the binary code word; linking two other binary code words with the signals so as to obtain two digital signals of two dark transmit channels which are determined by the two other binary code words; extracting, on the basis of the digital signal of the bright transmit channel and of the two digital signals of the dark transmit channels, a value of a magnitude indicating the physiological parameter, the extracting including forming a differential signal from the two dark channels, and an aliasing interference in the digital signal of the bright transmit channel being reduced by means of a spectral analysis of the differential signal.

According to another embodiment, an apparatus for generating a light signal for coupling into a body part may have: a driver for generating a drive signal, the driver being implemented to generate a series of iterating sequences, and wherein a sequence includes at least two bright periods, wherein the drive signal causes an on state of a light source, and at least two dark periods during which the drive signal causes an off state of the light source, and the at least two bright periods being irregularly arranged within the sequence; at least one light source for generating the light signal on the basis of the drive signal; and a securer for securing the light source to the body part.

According to another embodiment, a method of generating a light signal for coupling into body parts may have the steps of: generating a drive signal, the drive signal including a series of iterating sequences, and a sequence including at least two bright periods, wherein the drive signal causes an on state of a light source, and at least two dark periods during which the drive signal causes an off state of the light source, and the at least two bright periods being irregularly arranged within the sequence, and generating the light signal, on the basis of the drive signal, for coupling into a body part.

The object is achieved by an apparatus for determining a physiological parameter of a living being, comprising a receive means adapted to receive iterating optical signals and convert them to electrical signals, an optical signal including sequences, and a sequence comprising at least two bright periods during which a transmit light source adopts an on state and at least one dark period during which no transmit light source adopts an on state, and the at least two bright periods being irregularly arranged within a sequence. In addition, the apparatus comprises an extraction means for extracting information on the physiological parameter from the receive signal, the extraction means being adapted to extract, on the basis of the information on the arrangement of the bright periods within the sequence, a value of a magnitude indicating the vital parameter.

In addition, the object is achieved by an transmit device for generating a light signal for coupling into a body part, adapted to generate a drive signal using a driver means, the driver means being implemented to generate a series of iterating sequences, and wherein a sequence comprises at least two bright periods during which the drive signal causes an on state of the light source, at least one dark period during which the drive signal causes an off state of all of the light sources, and the at least two bright periods being irregularly arranged within the sequence, and at least one light source for generating a light signal, on the basis of the drive signal, for coupling into a body part.

The core idea of the present invention is to control a light source whose light is coupled into a part of a subject's body, and the signal received by a photodetector such that the light source adopts, within an iterating sequence, the on state at irregular intervals. The irregularity causes an expansion to occur within the spectral range of the signal. The additional spectral components of the light signal give rise to additional interference immunity. In the simplest case, two spectral lines of the same level will arise. Since the probability that both spectral components will be interfered with at the same time is smaller than the probability that a single spectral component will be interfered with, a diversity gain arises in the frequency range. This diversity gain may be implemented by corresponding signal processing, so that increased interference immunity and, thus, increased reliability of the measurement of a physiological parameter is achieved by the irregular control of the light sources. In addition, a so-called spread gain results. By the irregular controlling, the energy of the useful signal is evenly distributed to several frequency portions. Since the irregularity is known, these energy portions may again be coherently overlaid within the receiver. Interference portions having the same frequencies are also overlaid within the receiver; however, since same are interdependent, a coherent overlay takes place here, so that a gain results for the useful signal. A narrow-band interferer which overlays the useful signal only at one frequency portion will experience, within the receiver, a spectral expansion which is analogous to that of the useful signal within the transmitter, since in both cases, signal portions are combined at irregular points in time.

Irregular controlling at the light source corresponds to a spread spectrum modulation. In combination with an adaptive filtering connected downstream, the spread spectrum modulation reduces signals portions which are to be attributed to ambient-light influences or electromagnetic interfering sources (e.g. high-frequency surgery). In addition, subsequent signal processing also enables a particularly efficient measurement of the oxygen saturation in the blood and of the heart rate of a patient, it also being possible with the present method to perform reliable measurements even with a low arterial blood volume pulsation and while the patient is moving. Thus, the increased reliability of the measurement directly causes an increase in the quality of treatment for a patient. Thus, one advantage of the present invention is the fact that due to the increased reliability of the measurement values of a pulse oximeter, in particular in critical environments such as operating rooms or intensive-care units, increased chances of recovery and more efficient methods of treatment are enabled.

BRIEF DESCRIPTION OF THE DRAWINGS

Embodiments of the present invention will be detailed subsequently referring to the appended drawings, in which:

FIG. 4 is a schematized representation of a spectrum of a signal within the baseband FIG. 5 is a schematized representation of a spectrum of a signal within the transmission band FIG. 15a shows an exemplary waveform of an input signal and of the low-pass filtered DC signal (DC portion)

FIG. 15b shows an exemplary waveform of the high-pass filtered signal (AC portion)

DETAILED DESCRIPTION OF THE INVENTION

Figure 1:
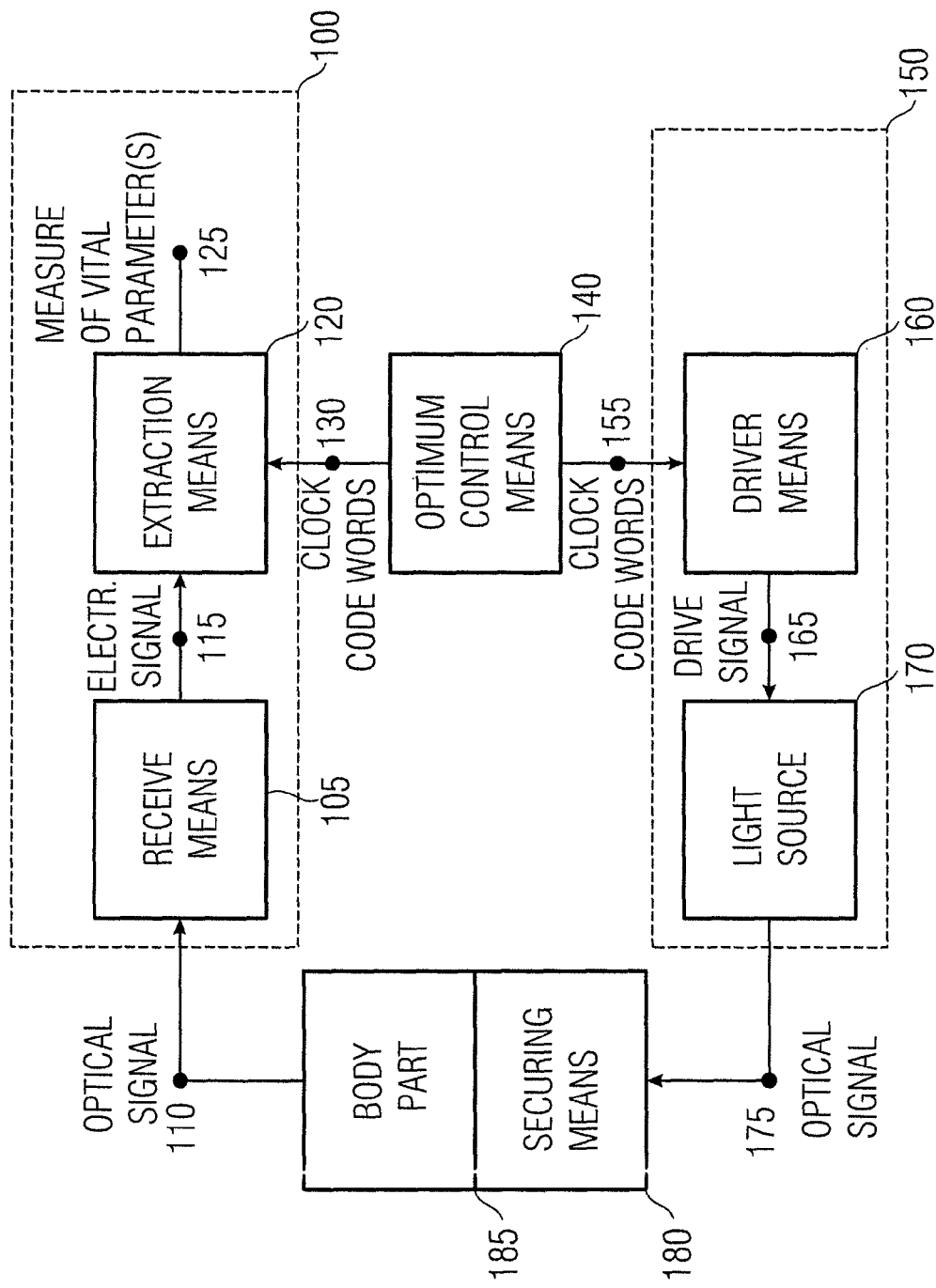
FIG. 1 is a fundamental block diagram of the advantageous embodiment

FIG. 1 shows a block diagram of an inventive embodiment consisting of a receiver 100 and a transmitter 150. The receiver 100 comprises a receive means 105 which receives sequences of optical signals at its input 110 and emits same as converted electrical signals at its output 115. The receive means 105 has the extraction means 120 connected downstream from it on the output side. The extraction means 120 receives the electrical signals of the receive means 105 at its input 115, extract therefrom a measure of a physiological parameter, such as heart rate or blood oxygen saturation, and emits same at its output 125. Optionally, the extraction means 120 receives a clock at a control input 130, and the extraction means 120 may optionally also receive, via the control input 130, additional information, e.g. in the form of binary code words which contain information on the temporal position of the time periods belonging to a transmit channel.

In principle, the clock may also be generated by the extraction means 120 itself, for example by analyzing the receive signal or by an integrated clock generator. Optionally, the apparatus described comprises a control means 140 which may predefine a clock for the extraction means 120 via the control input 130 thereof. Optionally, the control means 140 may also predefine a clock for the transmitter. In this manner, synchronization is achieved between the transmitter 150 and the receiver 100. This clock is then possibly passed on to a driver means 160 via a control terminal 155. The driver means 160 provides, at an output 165, a drive signal which is passed on to a light source 170. The light source 170 converts the drive signal to an optical signal and provides same at an output 175. For example, the optical signal may be coupled into a part of the body of the subject 185 via a securing means 180.

Figure 2A:
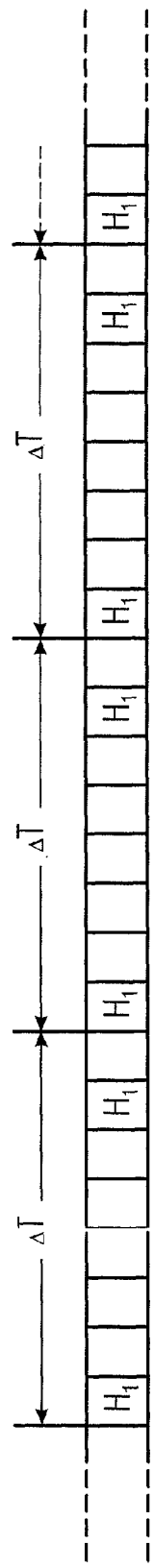
FIG. 2a is a schematic representation of the irregular arrangement of the bright periods
Figure 2B:
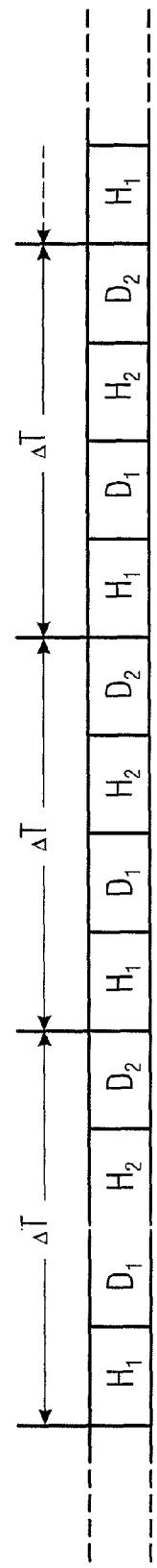
FIG. 2b shows a regular arrangement of the bright periods in accordance with conventional pulse oximeters

The driver means 160 controls the light source 170 with iterating electrical signals containing sequences, the sequence being composed of bright periods, wherein the light source 170 adopts the on state, and dark periods, wherein the light source 170 adopts the off state. The driver means 160 is designed such that the bright periods within the sequence are irregular. This irregularity of the bright periods is depicted in FIG. 2a in a schematized manner. FIG. 2a shows an iterating sequence of a duration of ΔT. Within one sequence, a light source $H_1$ adopts an on state twice. This is indicated in FIG. 2a by the entries $H_1$. During the other moments, when no entries are present within the time raster in FIG. 2a, the light source is switched off. For comparison, FIG. 2b depicts a sequence of a conventional pulse oximeter. FIG. 2b shows a time division multiple access method (TDMA), wherein two light sources are controlled. During one sequence, each light source adopts the on state for one time slot. This is indicated by $H_1$ and $H_2$ in FIG. 2b. During the other time periods, depicted by $D_1$ and $D_2$ in FIG. 2b (D represents "DARK"), none of the two light sourced is to have adopted an on state. The comparison of FIGS. 2a and 2b illustrates the decisive irregularity in the arrangement of the bright periods of the present invention.

Figure 3:
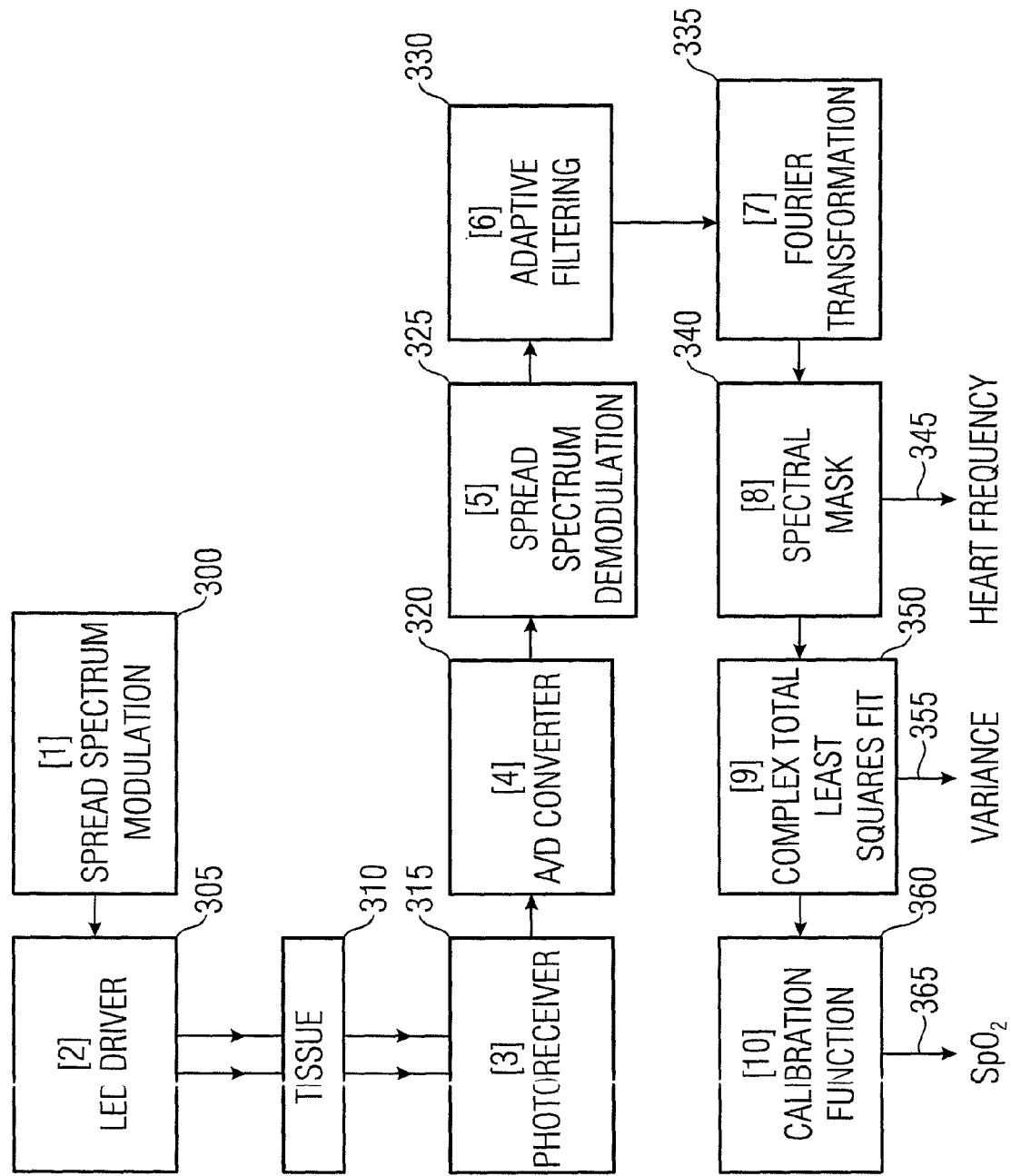
FIG. 3 is block diagram of an implementation of the advantageous embodiment

FIG. 3 shows an implementation of the advantageous embodiment. In FIG. 3, a spread spectrum modulation 300 is initially converted to an optical signal by an LED driver stage 305. In accordance with the spread spectrum modulation received, the LED driver means 305 couples light signals into a tissue 310 (e.g. into a finger), whereupon the light signals are modulated on their way through the tissue, and are subsequently received by a photoreceiver 315. Photoreceiver 315 converts the optical signals received to electrical signals and feeds same to an analog/digital conversion means 320 which converts the analog signal to a digital signal. The analog/digital conversion means 320 has a spread spectrum demodulator 325 connected downstream from it.

After the spread spectrum demodulation 325, the signal is adaptively filtered 330 and thereafter subject to a Fourier transformation 335. In a next step, a spectral mask 340 is now applied to the spectrum of the signal, whereupon the heart rate of the subject may be established and will then be output at an output 345. In a next analysis step, the so-called "complex total least squares fit" method 350, a variance of the difference of the different spectra which have been measured for light having different wavelengths may be determined, via a statistical analysis in the frequency range, and be output at the output 355 as a measure of reliability. Using the initial value provided by the "complex total least squares fit" means 350, an associated blood saturation value ($SpO_2$ value) may now be output, via a calibration function 360, at the output 365.

In order to be able to measure the light absorption of the tissue 310 with several light sources 305 having different wavelengths, and by means of a broad-band photoreceiver 315, a modulation method may be used, consisting of modulator 300 and demodulator 325. To better suppress interferences, the spread spectrum method is employed. This modulation method is based on the fact that because of the irregularity of the bright periods, the spectrum of the baseband signal is spread, or expanded. This effect is illustrated by FIGS. 4 to 9. Initially, FIG. 4 shows a spectrum $|I(f)|$ of a baseband signal, the cutoff frequency of which is referred to as $f_B$. With conventional modulation methods, such as amplitude modulation, the spectrum of the baseband signal is shifted into a frequency range more suitable for the transmission. FIG. 5 illustrates this case, and depicts the shifted spectrum $|I_A(f)|$. Such a spectrum results when the baseband signal is multiplied by a higher carrier frequency. The spectrum of the baseband signal remains unchanged in terms of its shape and energy. If this signal is overlaid by an interferer, it will not be possible to suppress this interference by demodulation, i.e. by means of a shift-back from the transmission band into the baseband. In the case of the spread spectrum modulation as is employed according to the invention, each transmit channel, which is understood to mean the transmit light signals of a wavelength, has a so-called chip sequence associated therewith which has been pre-computed. A chip sequence consists of a finite sequence of ones and zeros which are typically clocked in a frequency which is a hundred times higher than, by comparison, in a TDMA concept. The clock frequency is about 3 kHz. From a mathematical point of view, the chip sequences may meet certain characteristics in order to achieve the desired spreading action of the interfering signal, and to enable the reconstruction of the plethysmograms as well as of the ambient-light channels. In principle, the chip sequences may be orthogonal to be able to implement a channel separation in the demodulation, and so that a demodulation without any cross-talk is enabled.

Figure 6:
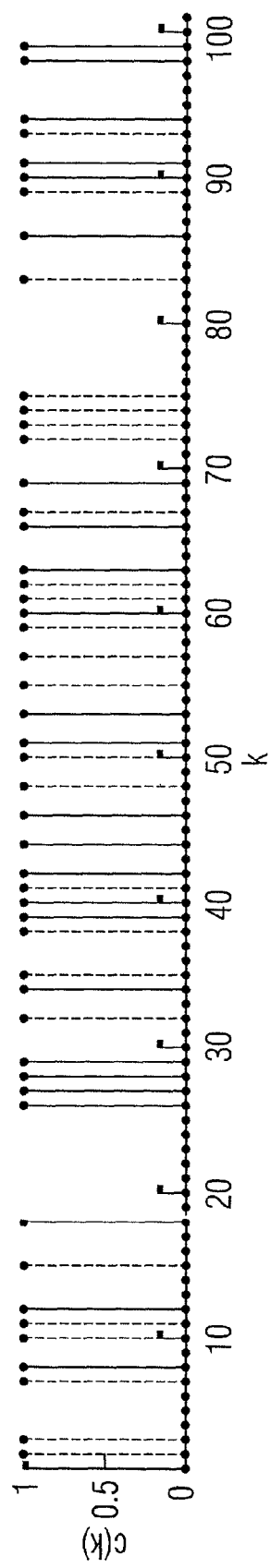
FIG. 6 is a schematic representation of two orthogonal chip sequences of a length of 101 chips

FIG. 6 shows a schematic representation of two orthogonal chip sequences, the length of a chip sequence equaling 101 chips. FIG. 6 depicts a time beam of a duration of 101 chip durations. The values of second chip sequences c(k) are plotted over these 101 chip durations. In the diagram, the two chip sequences are differentiated by dotted and solid lines, respectively. Whenever a chip sequence adopts a value of 1, this means that the light source associated is placed into the on state. It may be clearly seen in FIG. 6 that the two chip sequences are orthogonal, i.e. that the two associated light sources will never adopt the on state at the same time. FIG. 6 shows that the two chip sequences never adopt the value of 1 at the same time. In principle, it is also possible to employ chip sequences which simultaneously result in a 1, or it is possible to employ other sequences having other properties. Particular emphasis shall be placed, however, according to the invention, on the property of the sequences which causes the individual bright periods to occur at irregular intervals, so that the spectral spread according to the invention is achieved. In addition, it may be clearly seen in FIG. 6 that the individual bright periods within a sequence are arranged in an irregular manner, and that there are points in time when both chip sequences take on the value of 0, i.e. when both light sources are switched off in the implementation.

A further important property of the chip sequences is that their spectrum should be spread as evenly as possible, so that the signal energy will spread as evenly as possible to a frequency range as broad as possible.

Figure 7:
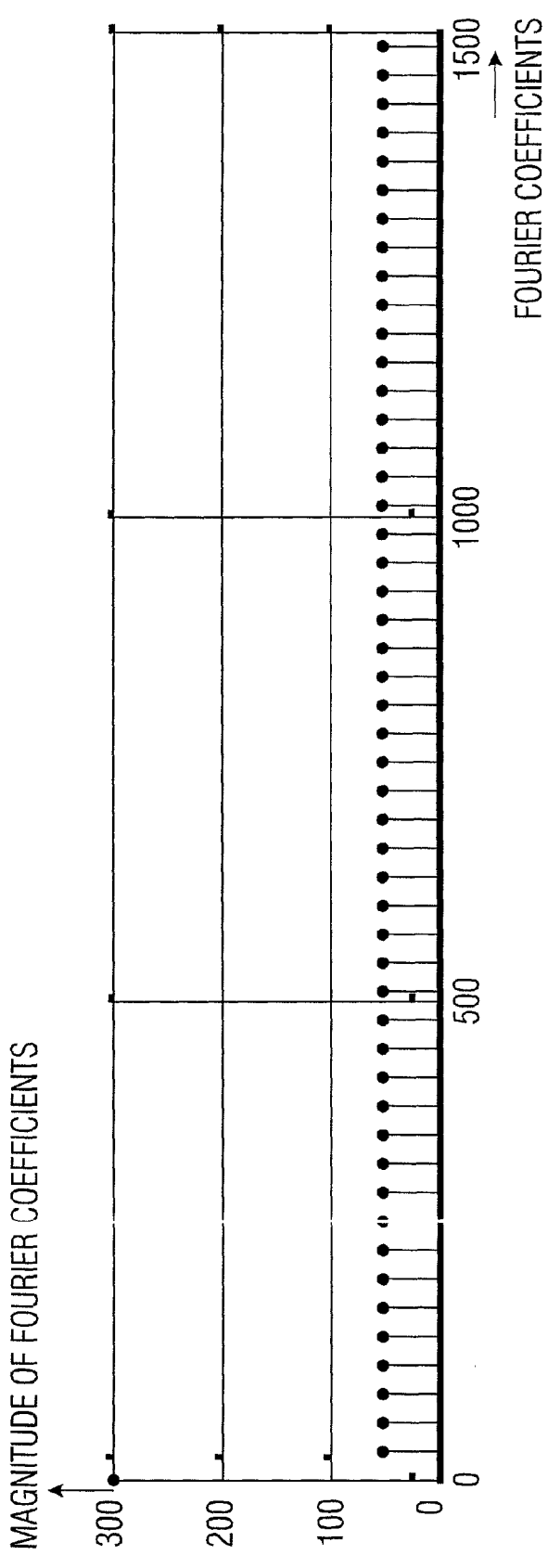
FIG. 7 is a schematic representation of a spectrum of a chip sequence of a length of 101 chips

FIG. 7 shows the spectrum, i.e. the frequency range, of one of the chip sequences depicted in FIG. 6. It may be clearly seen in FIG. 7 that the spectrum of such a sequence is evenly spread, i.e. the spectrum is composed of equidistant identical values. The high direct component represented by the excessive value at the frequency of 0, may be explained in that the chip sequence can only adopt the values of 0 and 1. Thus, the sequence is not free from a mean value. The spectrum of a chip sequence may therefore be regarded as a "comb" of equidistant carriers of identical amplitudes. The spectral equipartition of a chip sequence results in that a narrow-band interferer will be spread, after demodulation, into a broadband noise. In the implementation of the advantageous embodiment is depicted in FIG. 3, the two LEDs are controlled using the chip sequences depicted in FIG. 6.

Figure 8:
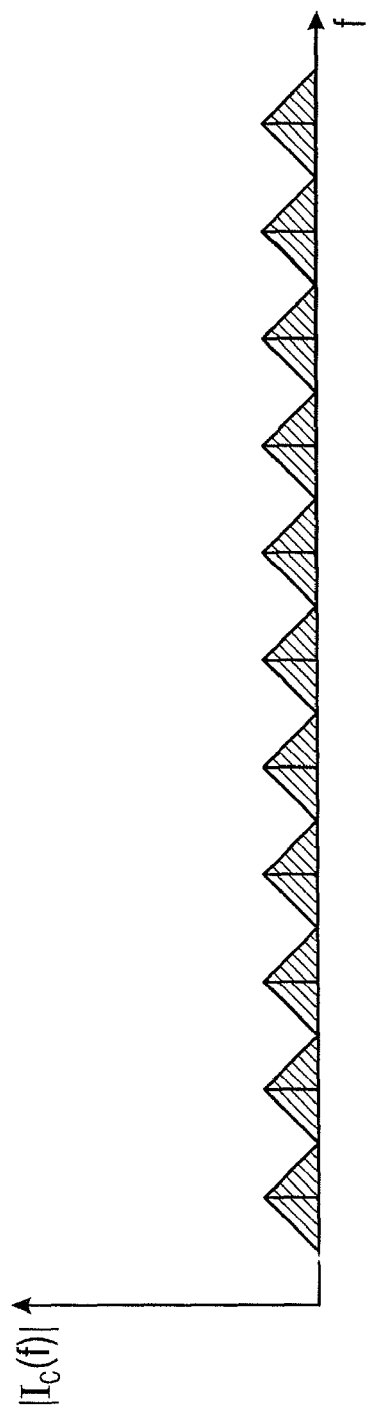
FIG. 8 is a schematic representation of the signal within the transmission band
Figure 9:
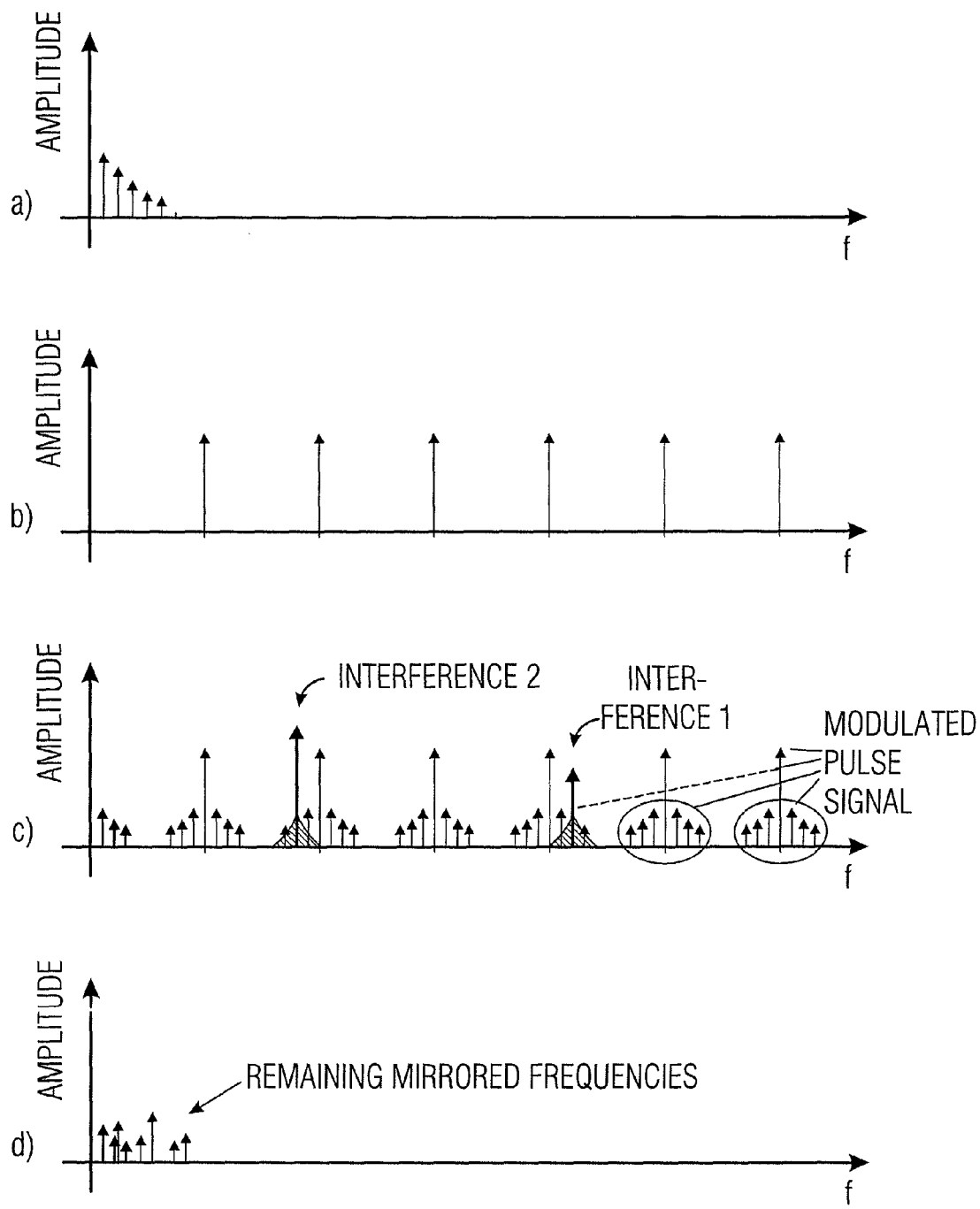
FIG. 9 is a schematic representation of the spread interference and de-spreading within the frequency range FIG. 9a) is a schematic representation of the spectrum within the baseband FIG. 9b) is a schematic representation of the spectrum of the chip sequence FIG. 9c) is a schematic representation of the spectrum within the transmission band FIG. 9d) is a schematic representation of the spectrum of the useful portions and interference portions within the baseband after de-spreading

FIG. 8 shows the schematic representation of the signal of FIG. 4 within the transmission band $|I_C(f)|$. The baseband signal, as is depicted in FIG. 4, maintains its spectral shape, but its energy is distributed to many frequencies. This process is also referred to as spreading. If the signal depicted in FIG. 8 is interfered with by a narrow-band interferer, said interferer will be subject to spreading in the demodulation, whereas the energy portions of the signal of FIG. 8 will again overlay one another in a coherent manner within the baseband. Here, the demodulation corresponds to a renewed multiplication by the respective chip sequence. The result of the multiplication is then summed up across a length of chip sequences. Thus, if a receive signal is multiplied by one of the chip sequences, as are depicted in FIG. 6, it may easily be seen from FIG. 6 that by the multiplication, only those receive signals values are masked out from the receive signal which are received at a moment which correspond to a one in the respective chip sequence. These individual signal portions are then summed up across a chip sequence, as a result of which they will coherently, i.e. constructively, overlay one another. An interfering signal which has overlaid the receive signal is also masked in only at the respective moments in time. Also, the interfering signals are sampled at the respective moments in time and are summed up across the length of chip sequence. However, the interfering signals do not coherently overlay one another at the sampling moments, so that they will actually experience a spreading across the de-spreading, i.e. the multiplication by the chip sequence, so that after demodulation, these signals will be present in an attenuated form only.

FIGS. 9a)-d) depict the operation of the spreading once again within the frequency range. FIG. 9a) shows the spectrum of a signal within the baseband. FIG. 9b) shows the spectrum of a chip sequence, the spectrum ideally being evenly distributed in spectral terms. FIG. 9c) shows the spread baseband signal which now has energy portions at each individual frequency of the chip sequence. The energy of the baseband signal has been spread to the frequencies contained within the chip sequence. In the inventive implementation, the signal is received in this form from the tissue by the photosensor, the actual useful signal then was modulated to the spread signal through the tissue. FIG. 9c) further depicts two interferences, "interference 1" and "interference 2". The two interferences are narrow-band interferers as may be caused, e.g., by fluorescent lamps or high-frequency scalpels. FIG. 9d) shows the spectrum of the signal after demodulation, or after de-spreading. It may be seen that the baseband signal has been reconstructed, and that additional frequencies of the interfering signals within the baseband have been added. FIG. 9d) also shows that the remaining frequencies of the interference have clearly smaller amplitudes than the original interference itself, which is due to the spreading of the interfering signal.

Legendre sequences are chip sequences which meet the characteristics useful here and which exhibit good auto and cross-correlation characteristics. In the contemplated implementation of the advantageous embodiment, the sequences modulate two bright transmit channels and two dark transmit channels. The spectral properties of all sequences are identical and meet the equidistribution useful within the spectral range. In addition, a total of four sequences are considered, the four sequences being orthogonal to one another, which means that no two sequences will adopt the value of 1 at the same time. In principle, the use of other sequences is also feasible, according to the invention the irregularity property of the bright periods is to be emphasized, this does not presuppose that at any moment in time, only one sequence may have a bright period. Two of the four sequences are used in an implementation of the advantageous embodiment to control two LEDs having different wavelengths (red and infrared), the two remaining sequences serve to modulate ambient-light channels, i.e. they correspond to dark channels.

Figure 10:
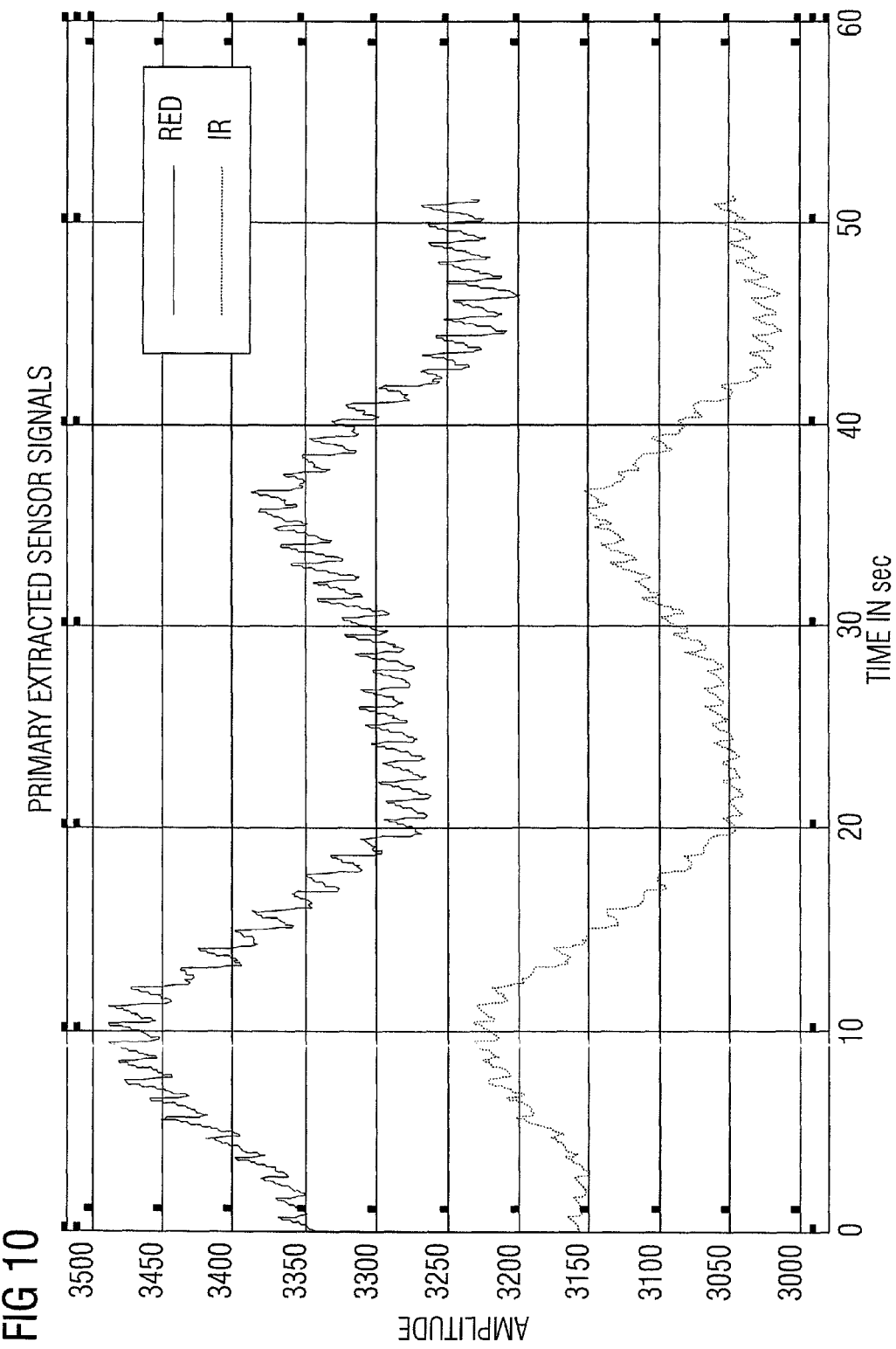
FIG. 10 shows two exemplary received waveforms of two LEDs having different wavelengths

The LEDs are now controlled as monochromatic light sources via LED driver 305 of FIG. 3. The light of the LEDs which is modulated with the chip sequences passes through a tissue layer, and depending on the wavelength of the light source, it experiences an adequate attenuation in the process. The radiation of the LEDs, which is attenuated by the tissue, impinges at photoreceiver 315, is converted to a proportional photocurrent there, and is subsequently sampled, while taking into account the Nyquist theorem, (sampling theorem) using an analog/digital converter 320, in a manner which is synchronous to the clock of modulator 300. The synchronicity between the modulator within the transmitter, and the AD converter and/or demodulator within the receiver may optionally be achieved by a control means which dictates clocks to both the transmitter and the receiver via control leads. The signal which has been synchronously sampled is fed to the spread spectrum demodulator 325. By means of the demodulation, spread spectrum demodulator 325 divides the signal of the photoreceiver up into individual channels. In a practically oriented implementation, these are two pulse channels for red and infrared LEDs, as well as two channels for measuring the ambient light. FIG. 10 shows two exemplary waveforms, the lower one corresponding to the red LED, and the upper one to the infrared LED. It may be seen in FIG. 10 that both signals are overlaid by a higher-frequency signal portion originating from the pulse signal of the subject, that both signals have a high direct component, and that both signals have a low-frequency interfering portion which may have been caused, for example, by changes in ambient light due to movements on the part of the subject.

Figure 11:
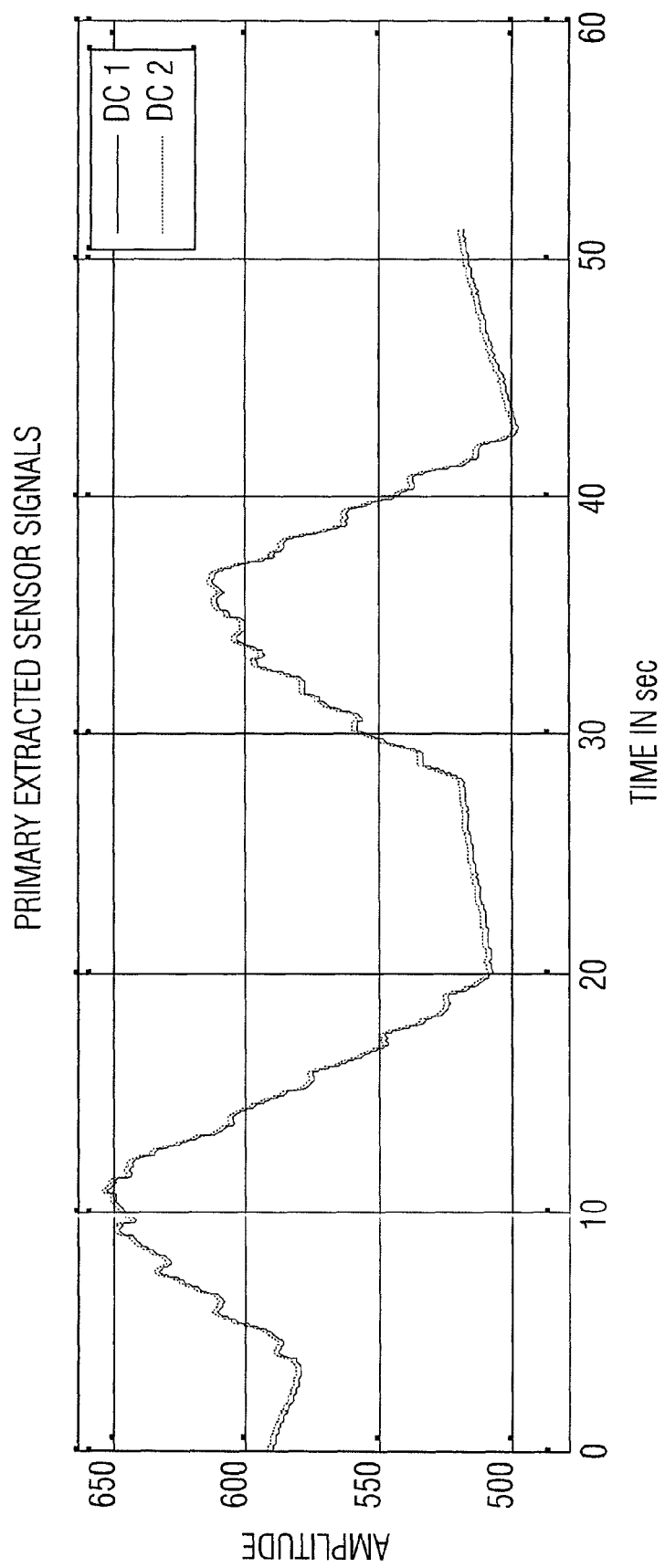
FIG. 11 is a representation of two exemplary waveforms for the dark duration and the ambient-light measurement, respectively

FIG. 11 shows two exemplary waveforms for the two dark channels. In these two signals, too, it is possible to recognize the high-frequency portion originating from the pulse signal of the subject, as well as an interfering portion to be attributed to ambient-light changes. The direct component in FIG. 11 is correspondingly smaller than the direct component in FIG. 10, since both light sources are switched off during the dark channel phases. In order to specifically calculate, and extract, the influences of the ambient light from the bright transmit channels, the mean value of the two ambient-light channels is subtracted from the two bright transmit channels so as to remove that portion of ambient light which is below the two sampling frequencies from the signal measured.

For demodulation purposes, a so-called matched filter is used, for each chip sequence, for extracting the transmit channels from the receive signal. Such a matched filter is an implementation of the spread spectrum modulator 325 of FIG. 3 and may be described as a mathematical operation with a chip sequence. The sensor signal is cyclically multiplied by the chip sequence, and the result is summed up over one chip-sequence length in each case. In the realization of the advantageous embodiment which is described here, these are the respective Legendre sequences. Mathematically speaking, the matched filter implements a scalar product between the chip sequence and the receive vector, i.e. the sampled receive signal. Transmitter and receiver are synchronized. The scalar product leads to blockwise de-spreading of a transmit channel into the baseband. What results at the same time is a subsampling with a factor which corresponds to the length of the chip sequence for the useful signal. To avoid aliasing, the bandwidth of the signal may be reduced prior to each subsampling operation. Thus, an anti-aliasing filter is useful which may be integrated, along with the matched filter, into one filter. The cutoff frequency of the combined filter may be cleverly selected so that no undesired aliasing effects occur during sub-sampling. Typically, there is a trade-off between the maximum passband and the smallest aliasing range.

Studies have shown that interferences having large amplitudes are mainly due to artificial illumination. In Europe, the mains frequency is 50 Hz, the fundamental wave of the power (or of the intensity) is therefore 100 Hz, and its harmonic waves correspondingly amount to multiples of 100 Hz. Depending on the intensity of the interference, the attenuation of the extraction filter within the stop band is not sufficient. On the basis of these findings, the frequencies corresponding to a multiple of 100 Hz may be suppressed by adjusting the properties of the extraction filter (combined filter).

Figure 12:
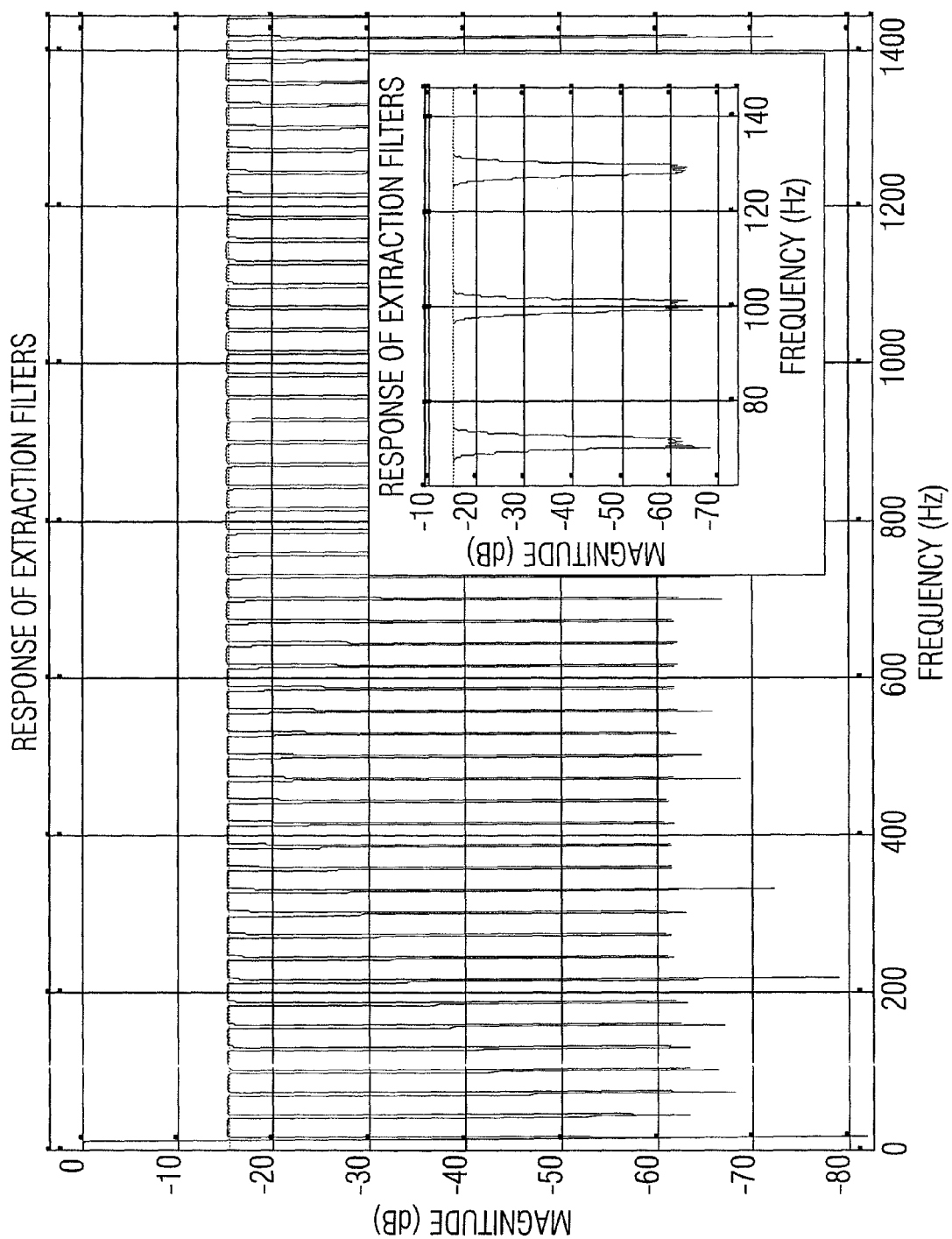
FIG. 12 depicts an exemplary transmission function of an extraction filter with an attenuation of 15 dB and a suppression of 100 Hz; enlargement in the area of 100 Hz

By way of example, FIG. 12 shows a transmission function of an extraction filter with an attenuation of 15 dB, wherein, additionally, the interferers are suppressed at multiples of 100 Hz. Thus, the extraction filter already includes a low-pass filter useful for subsampling, and at the same time a matched filter for de-spreading the spread signal from the transmission band into the baseband. A filter which implements subsampling is also referred to as a subsampler, the matched filter for de-spreading the spread signal is also referred to as a correlator, since it correlates a predefined chip sequence with the receive signal.

After extraction from the receive signal, the extracted and subsampled signals are present. The degree of subsampling is dependent on the length of the chip sequence. A sample of the useful signal results for each chip-sequence length due to the matched filter. By using several orthogonal chip sequences, several channels result during a chip-sequence duration, in the inventive advantageous embodiment, there are four channels, two bright transmit channels of the red and infrared LEDs, as well as two dark transmit channels, during which none of the transmit light sources adopts an on state, and which are used for ambient-light and interference compensation.

In addition, the interferences present above the useful band, i.e. interferences present above half the sampling frequency, are mirrored into the useful band at 15 dB by the extraction filter. The attenuation of the interferences above half the sampling frequency depends on the chip-sequence length. In the inventive realization of the advantageous embodiment, a chip-sequence length of 101 chips has been selected, which leads to an attenuation of 15 dB for interferences above half the sampling frequency. At the same time, the filter implements additional attenuation of all frequencies comprising a multiple of 100 Hz. FIG. 12 shows an exemplary transmission function of an extraction filter.

After the extraction filter, the useful signals are present within the baseband. To reduce the influence of the ambient light the ambient-light portion is subtracted from the useful signal, in addition, a reference signal is generated for the adaptive filter 330 connected, on the output side, downstream from the spread spectrum modulator 325. For ambient-light subtraction, a mean value is initially formed from the dark channels, which is then subtracted from the bright transmit channels. Depending on the type of chip sequences used, and/or depending on the configuration of the spectra of the individual chip sequences, it may be advantageous not to determine the exact mean value of the dark channels, but to linearly weight the dark channels. In the implementation of the inventive advantageous embodiment, Legendre sequences of the length of 101 chips are used. This implementation resulted in an optimal weighting of the dark channels of from 47.5% to 52.5%.

For the purposes of further inventive signal processing, it is important to differentiate between two frequency bands into which an interferer may be categorized. On the one hand, the band exists below half the sampling frequency, the useful band. On the other hand, the band exists above this frequency, the transmission band. Frequency components which are due to interference and are categorized into the useful band may be removed from the two useful signals (bright transmit channels of the red and infrared LEDs) by means of dark-phase subtraction. The signals of these frequencies are equal both in phase and in amplitude, and therefore do not appear in the difference of the two dark channels, the reference signal. An interferer within the useful band (or the baseband) will thus continuously result in 0 for the reference signal. An interferer within the useful band could be a light source which is detected by the photosensor through the tissue, and the intensity of which is modulated with the changes in volume of the arterial blood. However, these portions are not to be filtered out from the useful signal, as they contain the information desired (the pulsatile portion).

Figure 13:
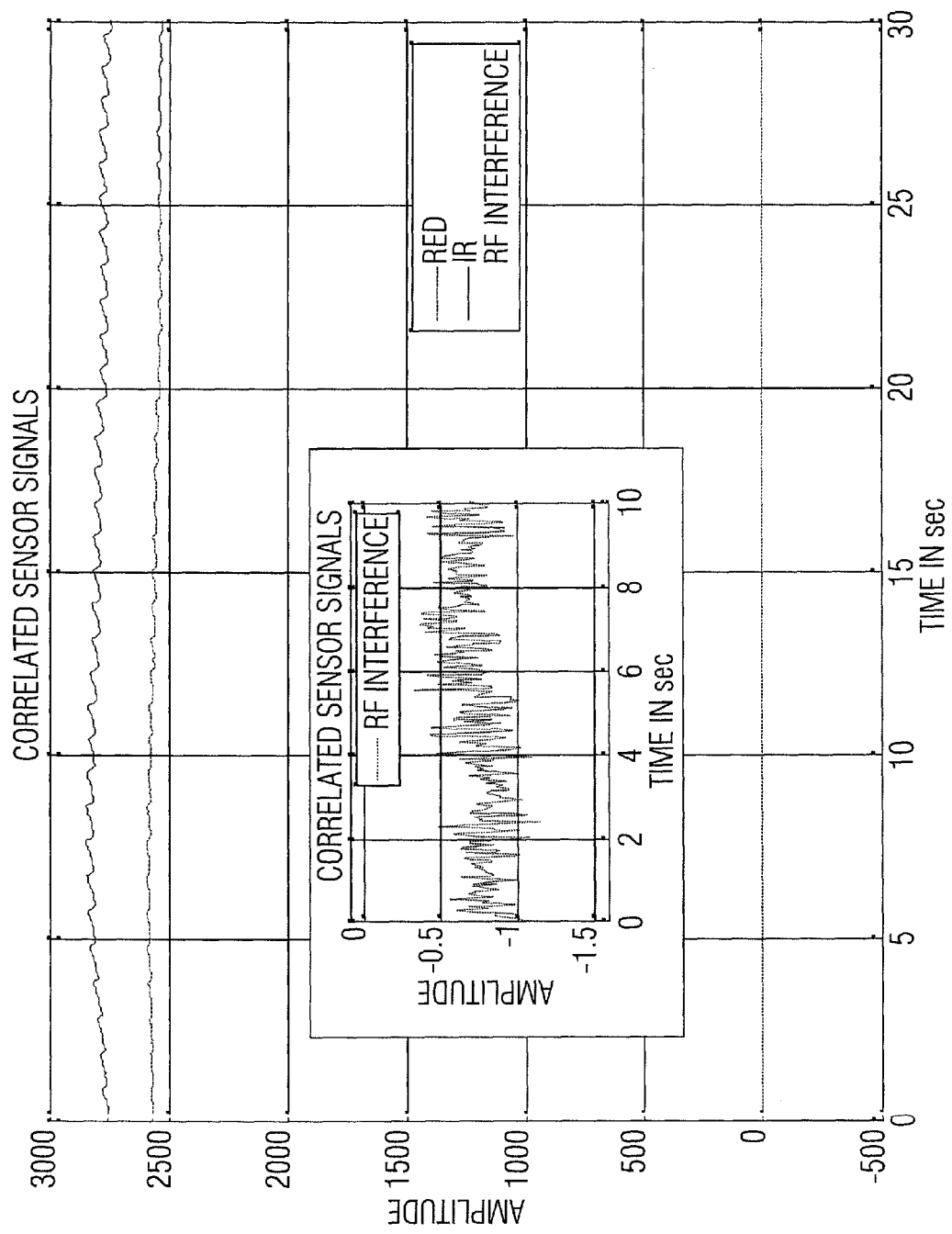
FIG. 13 depicts exemplary waveforms of the bright transmit channels from which the ambient-light signal has been subtracted, the enlargement shows the reference signal

By contrast, an interferer could be categorized into the transmission band. In this case, the attenuation of the extraction filter will set in, which initially causes the interference to fall into the useful band in an attenuated state. In the implementation of the advantageous embodiment, this attenuation amounts to 15 dB. In addition, signals of these frequencies are subject to a phase shift which is different for each channel. Thus, the difference between the two dark transmit channels (the reference signal) does not result in an extinction of these signals, but results in a signal, the frequency components of which contain the mirrored frequencies of the interferer from the transmission band. This signal now serves as a reference signal for an adaptive filter 330, so as to reduce the remaining interferences from the transmission band as well. The ambient-light subtraction thus removes the interferences from the useful band, but also contains phase-shifted interfering portions from the transmission band. Once the interferences from the transmission band have experienced attenuation by the extraction, portions of this interference are now re-fed to the useful signal by the ambient-light subtraction. Therefore, what results is not the full attenuation for the interfering signals from the transmission band, but a smaller value. In the implementation of the inventive advantageous embodiment, the attenuation of the extraction filter initially amounts to 15 dB, but is reduced again by 3 dB by the ambient-light subtraction, so that a total attenuation of 12 dB results for interferers from the transmission band. FIG. 13 shows two exemplary waveforms for the two transmit channels, red and infrared LEDs, from which the ambient-light signal has been subtracted. In addition, FIG. 13 shows an exemplary reference signal in a magnified form.

Figure 14:
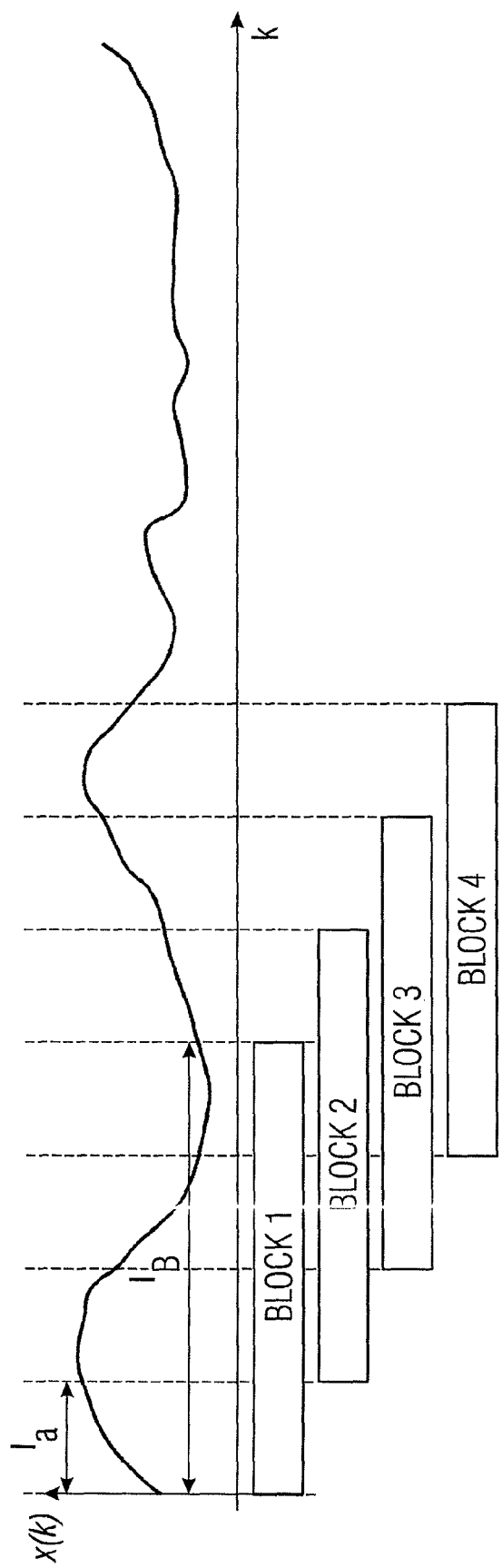
FIG. 14 is a schematic representation of the block formation for further signal processing, $l_B$ corresponds to the block length, $l_a$ is a measure of the overlap

For further signal processing, a block formation for the individual signals initially occurs. For this purpose, the signals are divided up into blocks of equal lengths, the individual blocks overlapping. FIG. 14 illustrates the block formation for further signal processing. Blocks of a length of $l_B$ are formed from the samples of a useful signal, a new block being formed every $l_a$ samples.

The useful signals are subsequently fed to a frequency-separating means. It is the task of the frequency-separating means to filter the direct component and the pulsatile portion from the input signals. In the implementation of the inventive advantageous embodiment, the separating frequency of the frequency-separating means amounts to about 0.5 Hz. FIG. 15a shows the exemplary curve of an input signal being fed to the frequency-separating means. In addition, FIG. 15a depicts the low-pass filtered portion (DC portion) of the input signal. FIG. 15b) depicts the associated high-pass portion (AC portion) of the input signal. Further signal processing only relates to the high-pass portion of the input signal.

The high-pass filtered useful signals are now fed to an adaptive filter 330. It is the task of the filter, also referred to as interference canceller, to remove interferences which were present in the transmission band and were mirrored, after extraction, into the useful band in an attenuated state, cf. FIG. 9d. The reference signal which contains the frequencies of the interference in the useful band has been removed from the dark transmit channels. The reference signal differs in phase and amplitude from the interferences overlaid on the useful signals. It is therefore the task of the adaptive filter to filter out the undesired image frequencies from the useful signals using the reference signal. For this purpose, an interfering signal is constructed, from the reference signal, which is as close as possible to the interference overlaid upon the useful signal. There are several mathematical methods of determining the coefficients for adaptive filter 330. One known method would be to select the coefficients of adaptive filter 330 such that the deviation between the reference signal and the useful signal is minimized. For determining the coefficients, the complex total least squares fit method, is also to be mentioned here.

Figure 16:
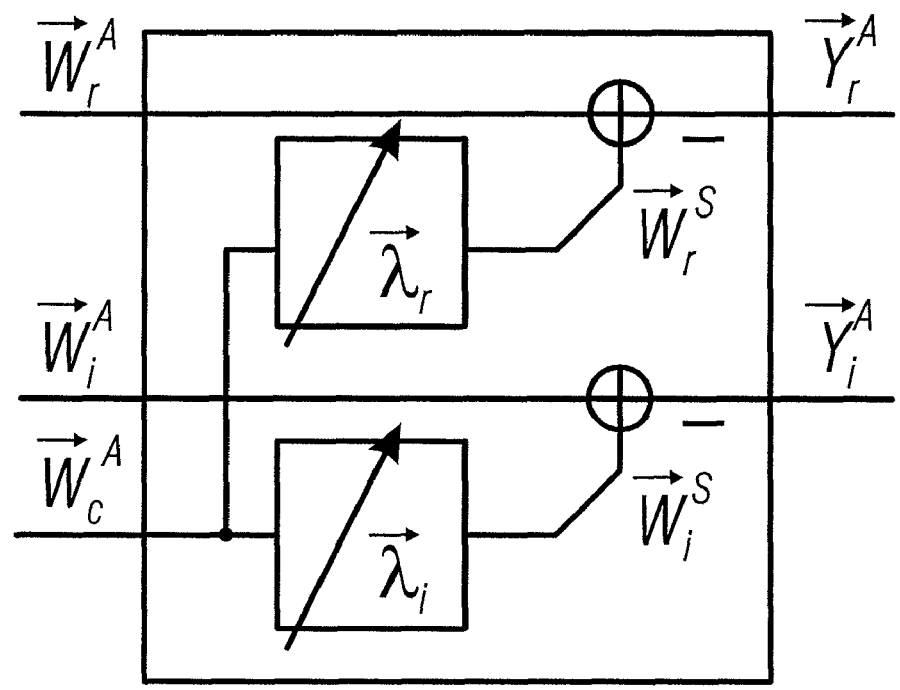
FIG. 16 depicts a model of the adaptive filter, with the input quantities on the left and the output quantities on the right, the reference signal being designated by $W^A_c$

FIG. 16 shows the model of the adaptive filter with the input quantities $\vec{w}^A_r$ and $\vec{w}^A_i$ for the two input signals of the bright transmit channels for red and infrared, A indicating that the input signals are high-pass filtered. The reference signal is also high-pass filtered as $W^A_c$, and forms the basis for determining the adaptive filter coefficients $\vec{\lambda}_r$ and $\vec{\lambda}_i$. Using the adaptive filter, an interference vector is initially reconstructed, which are designated by $\vec{w}^S_r$ and $\vec{w}^S_i$ in FIG. 16. These interference portions are then subtracted from the useful signals, so that the useful signals $\vec{y}^A_i$ which have been corrected with regard to the interferences are present at the output of the adaptive filter.

Figure 17:
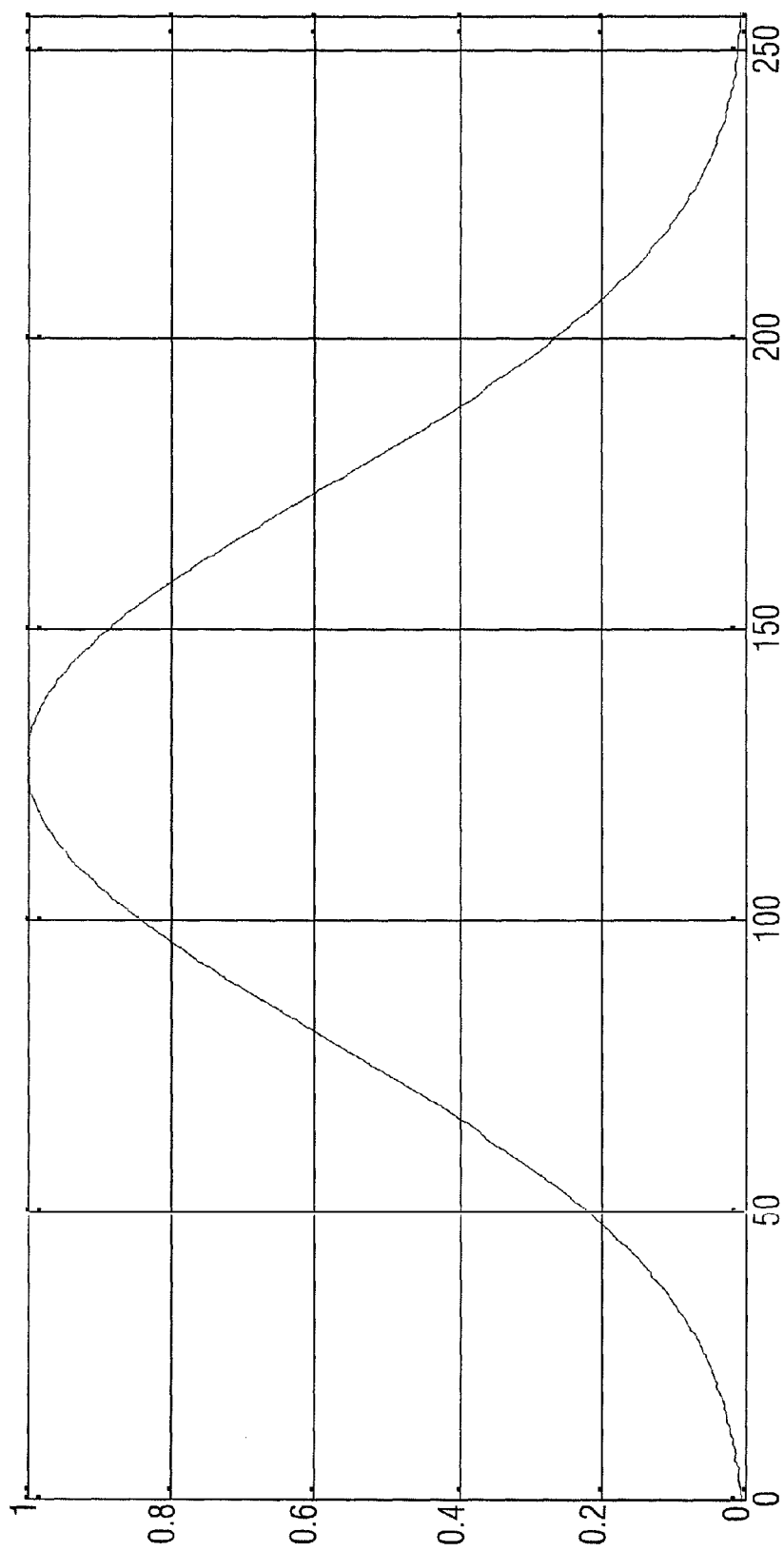
FIG. 17 depicts an exemplary curve of a Kaiser-Bessel window having a block length of 256 points

Since studies are subsequently performed in the frequency range, the input signals are transformed into the frequency range by means of Fourier transformation. Due to the block formation, unwanted side effects result in the frequency range. A block formation is to be equated with a multiplication of a rectangular pulse, which masks out the very block under consideration from a receive signal, by the receive signal itself. If this block is subject to Fourier transformation, one will obtain, in the frequency range, a convolution of the Fourier-transformed rectangular pulse (since function) with the actual spectrum of the sequence of receive signal samples. To reduce the unfavorable effects caused by the convolution with the sinc function in the frequency range, the block of receive signal samples is multiplied, in the time domain, by a window function having a narrower spectrum than the sinc function. For implementing the advantageous embodiment, a Kaiser-Bessel function is used for this purpose. FIG. 17 depicts the waveform of a Kaiser-Bessel window by way of example.

Figure 18:
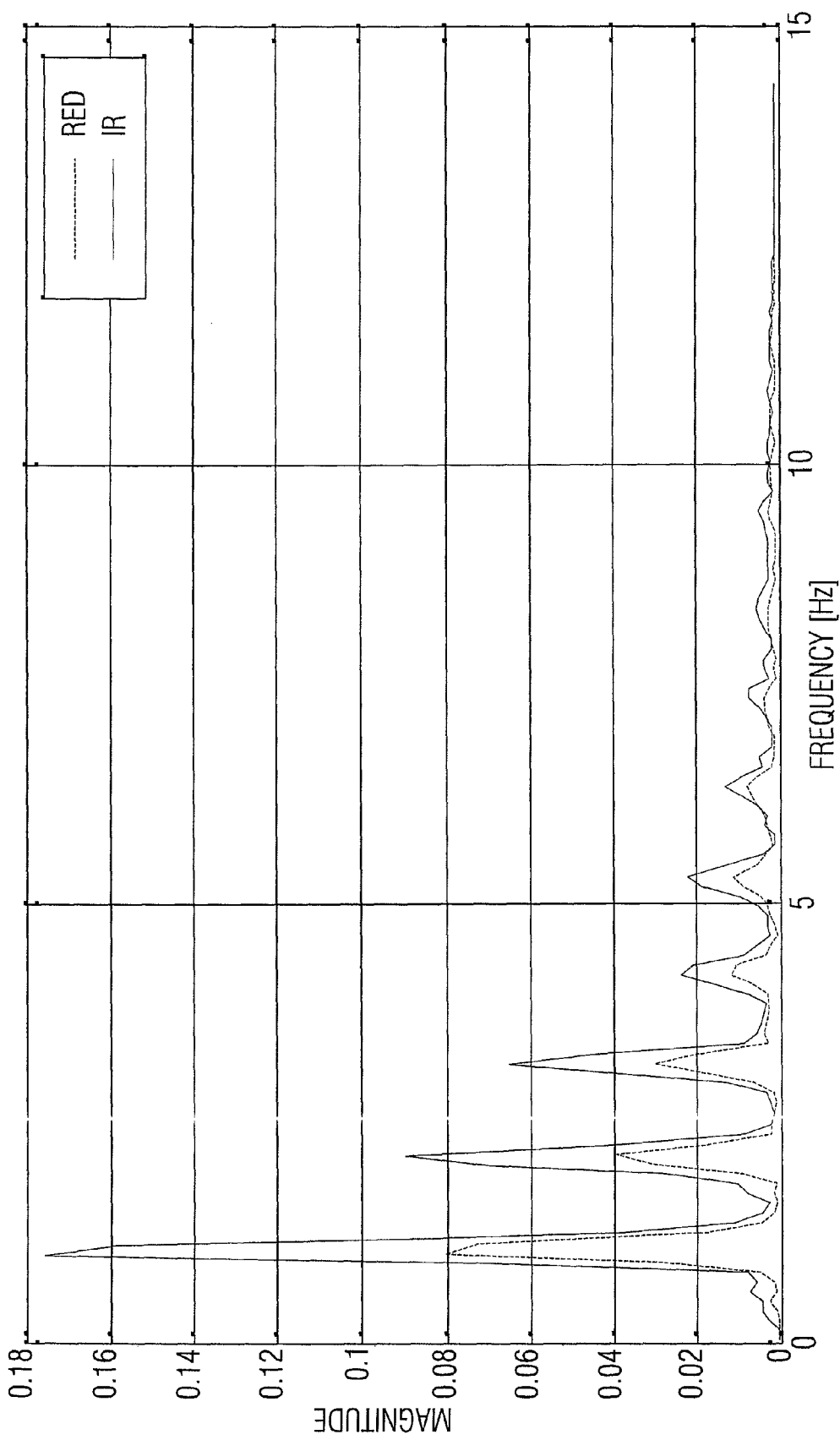
FIG. 18 is an exemplary spectral curve of the normalized useful signals for the two bright transmit channels, red and infrared

For further signal processing, the two useful signals are now normalized. Subsequently, the Fourier transformation is conducted. After the Fourier transformation, the spectra may be presented in different views, such as their curve as a function of time or as a function of the frequency. FIG. 18 shows exemplary spectra of the normalized signals from the bright transmit channels red and infrared. The spectrum shows a signal under good conditions, i.e. with relatively little interference. The Fourier transformation 335 is followed, in a next signal processing step, by applying a spectral mask 340 for determining the heart rate. The Fourier transformation of the two signals from the bright transmit channels initially provides two spectra. If the two signals were undisturbed, it would be possible to represent one of the two spectra as a linear combination of the other, respectively. However, since the two spectra comprise interferences, it is initially not possible to merge them into each other by a linear combination.

Figure 19:
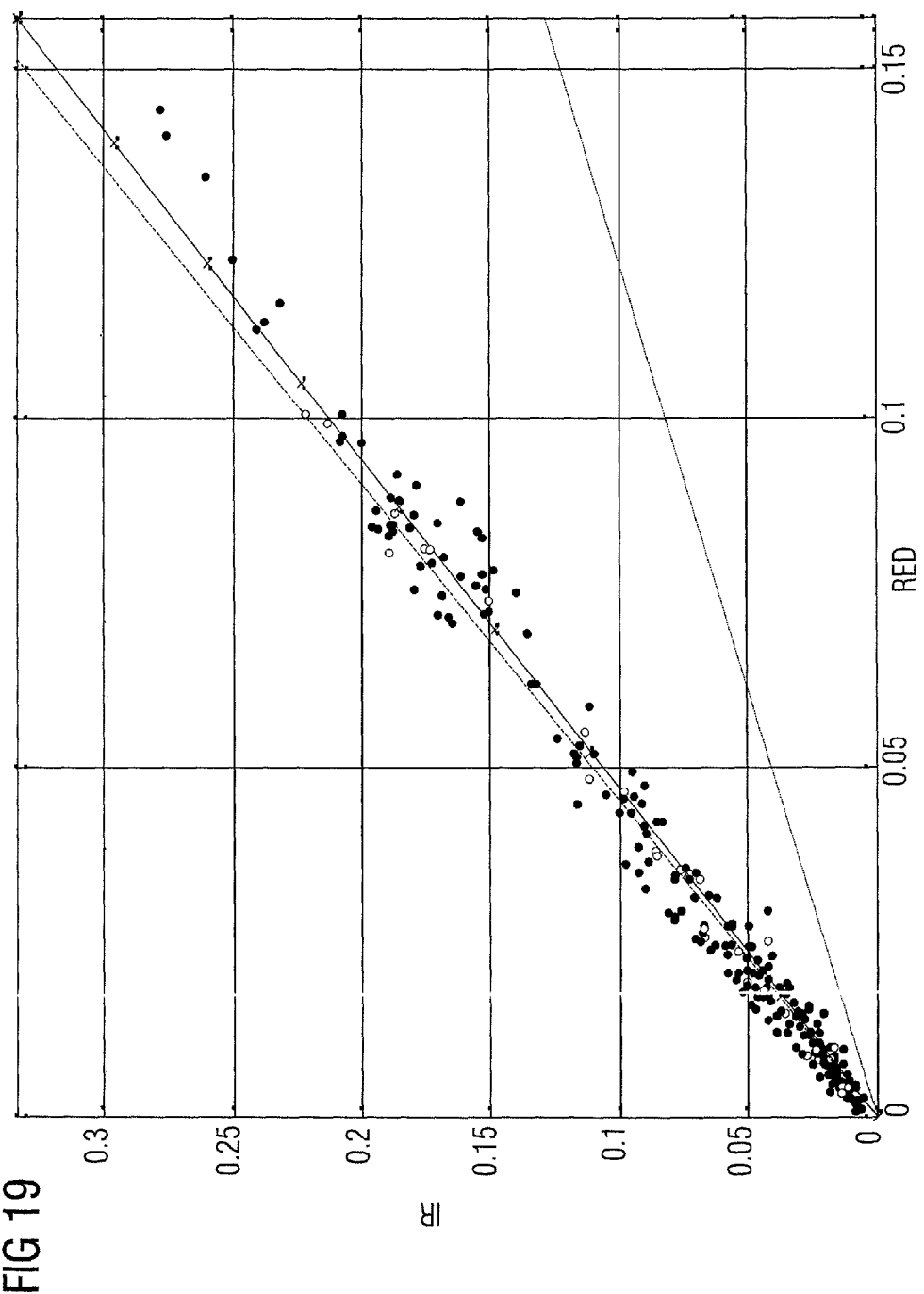
FIG. 19 is an exemplary representation of the two spectra for red and infrared transmit channels, spectral values of identical frequencies being plotted against one another

In FIG. 19, the two spectra for respectively identical frequency values are plotted against one another. One may see that the dots do not lie on a straight line, which would indicate a linear relationship between the two spectra. If the two spectra did not comprise any interferences, an original straight line would result with this representation. To solve this problem, an original straight line is now sought for using the method of the least squares fit, the sum of the square distances of all dots from this original straight line being minimized. This method is known by the synonym of the total least squares fit method.

Figure 20B:
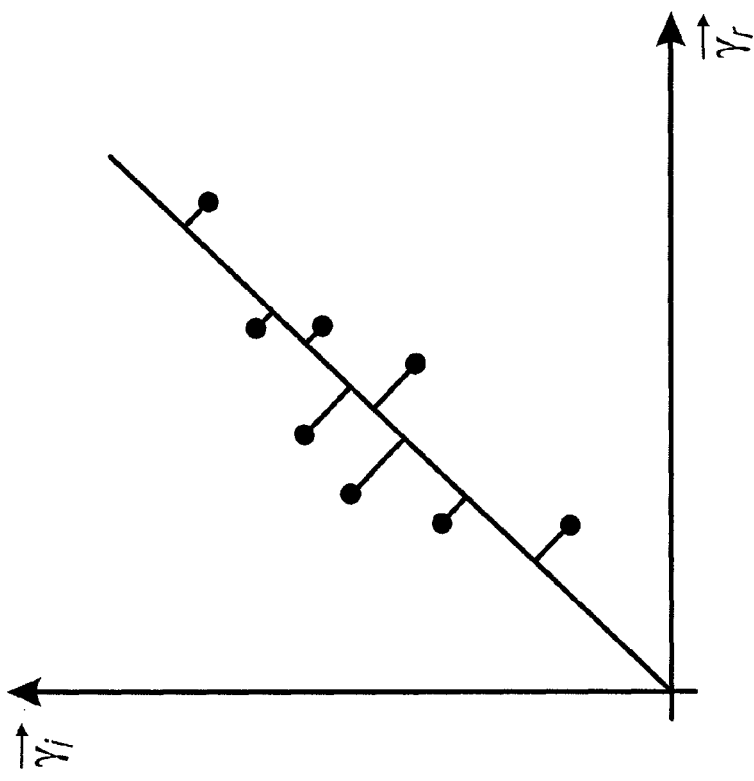
FIG. 20b is a schematic representation of the total least squares fit method for minimizing the actual distances from a straight line
Figure 20A:
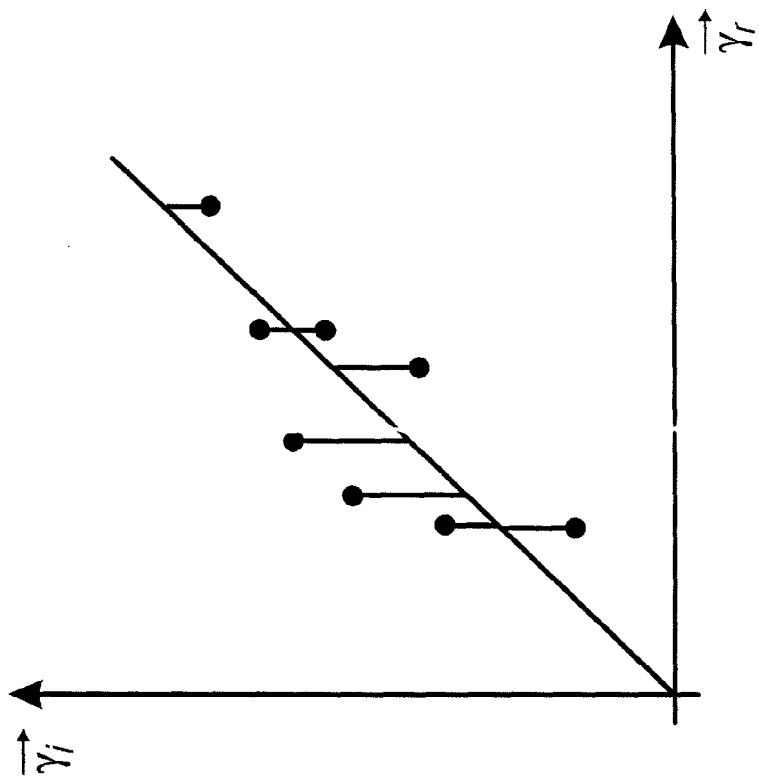
FIG. 20a is a schematic representation of the least squares fit method for minimizing a vertical distance from a straight line

FIG. 20a and FIG. 20b are to illustrate the approach in the total least squares fit method. Unlike the least squares fit method, which is depicted in FIG. 20a, in the total least squares fit method the actual distance of a dot from a straight line is minimized. This approach initially leads to an over-determined equation system. The over-determined equation system may be solved using a singular value decomposition so as to find a solution which corresponds to the total least squares fit method. Using the singular value decomposition, initially the matrix representing the over-determined linear equation system is decomposed. This results in a matrix containing, on its diagonal, the singular values of the equation system. By maintaining the maximum singular value, and by setting all other singular values to zero, this matrix is reduced to rank 1, and the problem is thus traced back to a solvable linear equation system. Such a straight solution line is drawn in in FIG. 19; it is located halfway between two other straight lines defining the range of values of valid slopes which result from the reference measurements of the SpO2 values. The slope of this straight line now represents a measure of the blood oxygen saturation of the subject. A reference spectrum may now be determined from the linear equation system which has been determined using the singular value decomposition.

The slope of the original straight line which has been determined in this manner may initially be distorted if a high-amplitude interference identically overlays in the two spectra. To reduce this type of interference, the spectral mask is employed. The function of the spectral mask 340 may be described as follows. In principle, it is a spectral method which browses the Fourier coefficients of the pulse signal within the spectrum so as to set all coefficients which do not belong to the pulse signal to zero. The principle of the spectral mask is based on the fact that the frequency components of the pulse wave differ from those of other interferers. The algorithm of the spectral mask fundamentally is a binary mask comprising the elements $\{0, 1\}$, by which the spectrum is multiplied on a point-by-point basis so as to suppress those Fourier coefficients which do not belong to the pulse signal.

Figure 21A:
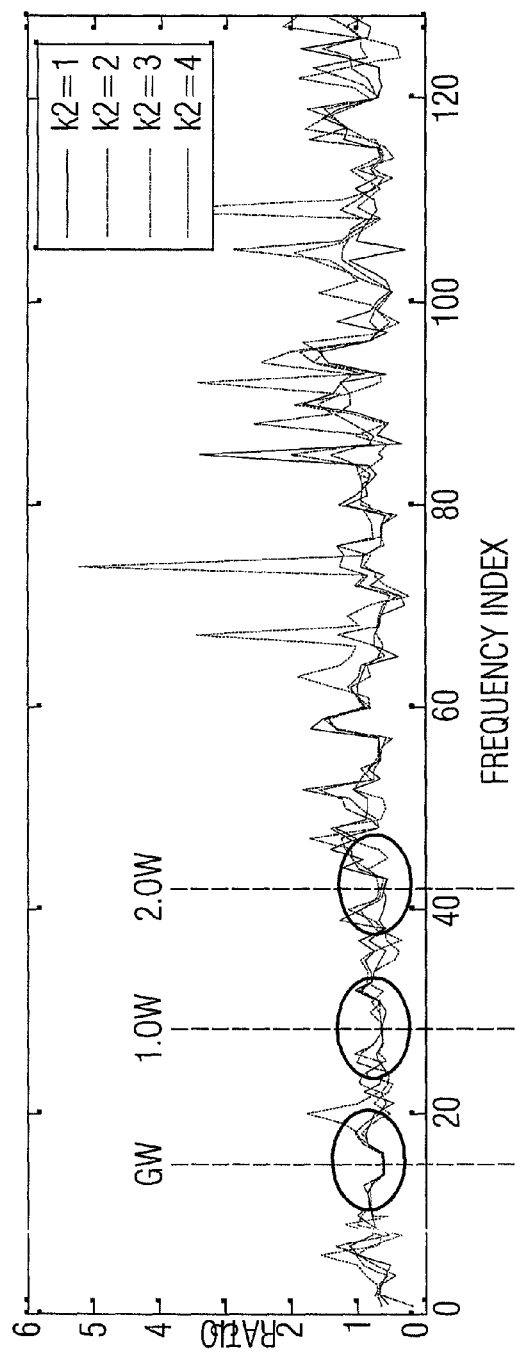
FIG. 21a depicts an exemplary curve of the quotient between the red transmit channel and the infrared transmit channel at four different points in time k2
Figure 21B:
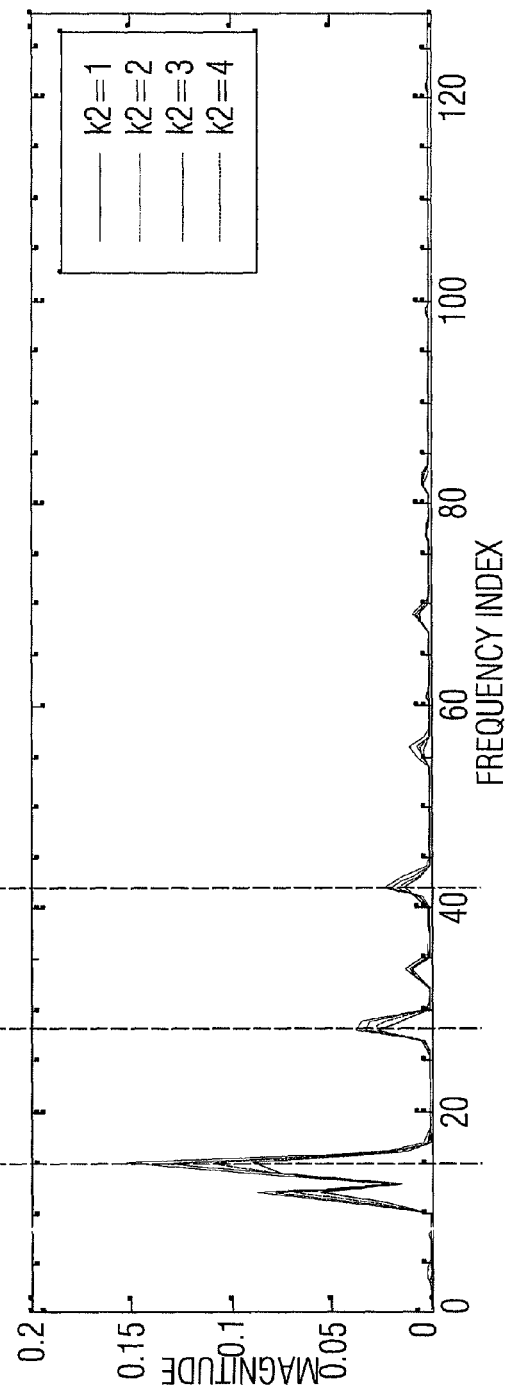
FIG. 21b shows an exemplary curve of a reference spectrum determined using the method of the complex total least squares fit method

FIG. 21a shows the exemplary curve of the quotient of two spectra of the waveforms of the bright transmit channels, FIG. 21b shows, in this context, the curve of a reference spectrum which has been corrected with regard to interferences. Both spectral curves are plotted at four different points in time, respectively, k2=1 . . . 4. If the quotient of the two spectra of FIG. 21a is compared to the reference spectrum across several time windows, it becomes clear that the quotient is correct only above the frequency components of the pulse signal, and is the same for all of these frequencies. Problem arise when the amplitudes of the interferences become larger than those of the pulse wave.

Figure 22:
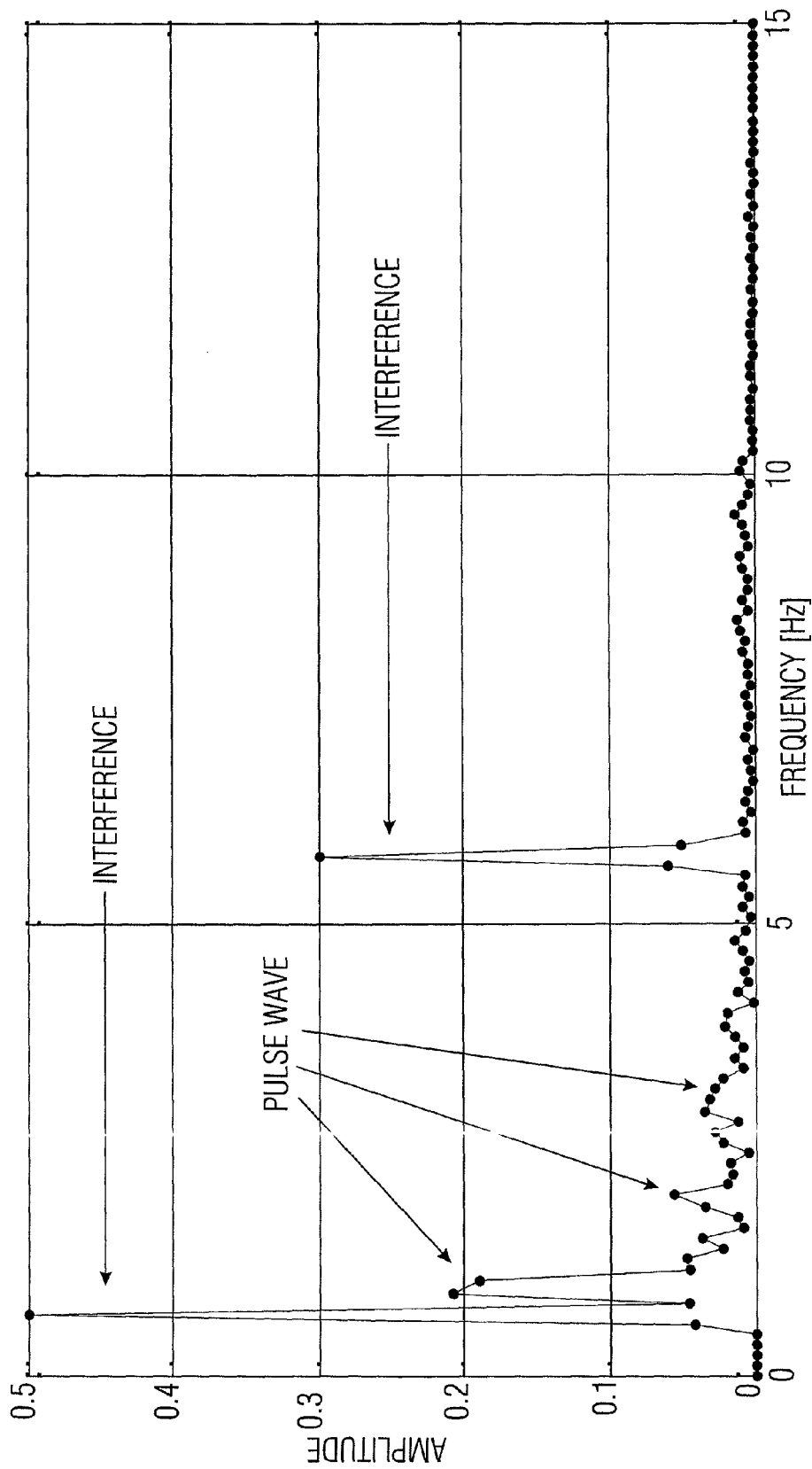
FIG. 22 depicts an exemplary spectrum of a waveform, wherein the amplitudes of the interference are larger than the amplitudes of the pulse wave

By way of example, FIG. 22a shows a spectrum of a signals disturbed by interfering signals, the amplitudes of which are larger than the amplitudes of the actual pulse wave. The quotient of two spectra is undefined at the frequencies of an interferer, and it bears no relation to the blood oxygen saturation of a subject. Without the spectral mask, dominant features would lead to an incorrect blood oxygen saturation value, as is shown in FIG. 22. Studies have shown that such dominant interferences mostly occur within both spectra, i.e. within the spectrum of the red signal as well as within the spectrum of the infrared signal. This results in that, in the quotient formation, quotients of a value of 1 arise. A quotient of a value of 1 corresponds to a blood oxygen saturation value of approx. 80%. It is now the task of the spectral mask to differentiate the frequency components of the pulse wave from those of the interferers.

The spectral mask exhibits an algorithm of the harmonic relation. The method of the harmonic relation is based on findings of examining numerous pulse signals for their spectral properties. The fundamental finding is the harmonic relation of the three relevant frequencies $f_g$ of the fundamental wave, $f_{o1}$ and $f_{o2}$ of the second harmonic. In this context, it is also known that the second harmonic is at double the frequency of the fundamental wave, and that the third harmonic is at three times the frequency of the fundamental wave. On the basis of this relation, a mask may now be created which masks in, in the frequency range, those frequency portions of double and three times the frequency of a fundamental wave, i.e. exhibits a 1 at these locations, and masks out all other frequencies, i.e. has a 0 at these locations. A sum may then be formed from the remaining coefficients, the sum being associated with the fundamental frequency. This process may then be repeated for any potential heart rates feasible, for example within a range from 30-300 Hz, and subsequently, that frequency at which the sum is maximized may be selected. A further property which may be taken into account in this context is that the amplitudes of the respective harmonics exhibit a decaying characteristic. This means that at the first harmonic or at double the frequency of the fundamental wave, the amplitude has a smaller amplitude than the fundamental wave itself. At the second harmonic, which has three times the frequency of the fundamental wave, the amplitude is smaller, in turn, than at the first harmonic. Values for which the appropriate condition of the decaying spectrum is not met will not be considered in the search for the maximum.

Now the heart rate may be determined via the position of the spectral mask. In the realization of the inventive advantageous embodiment of FIG. 3, the heart rate will be output at output 345.

Figure 23:
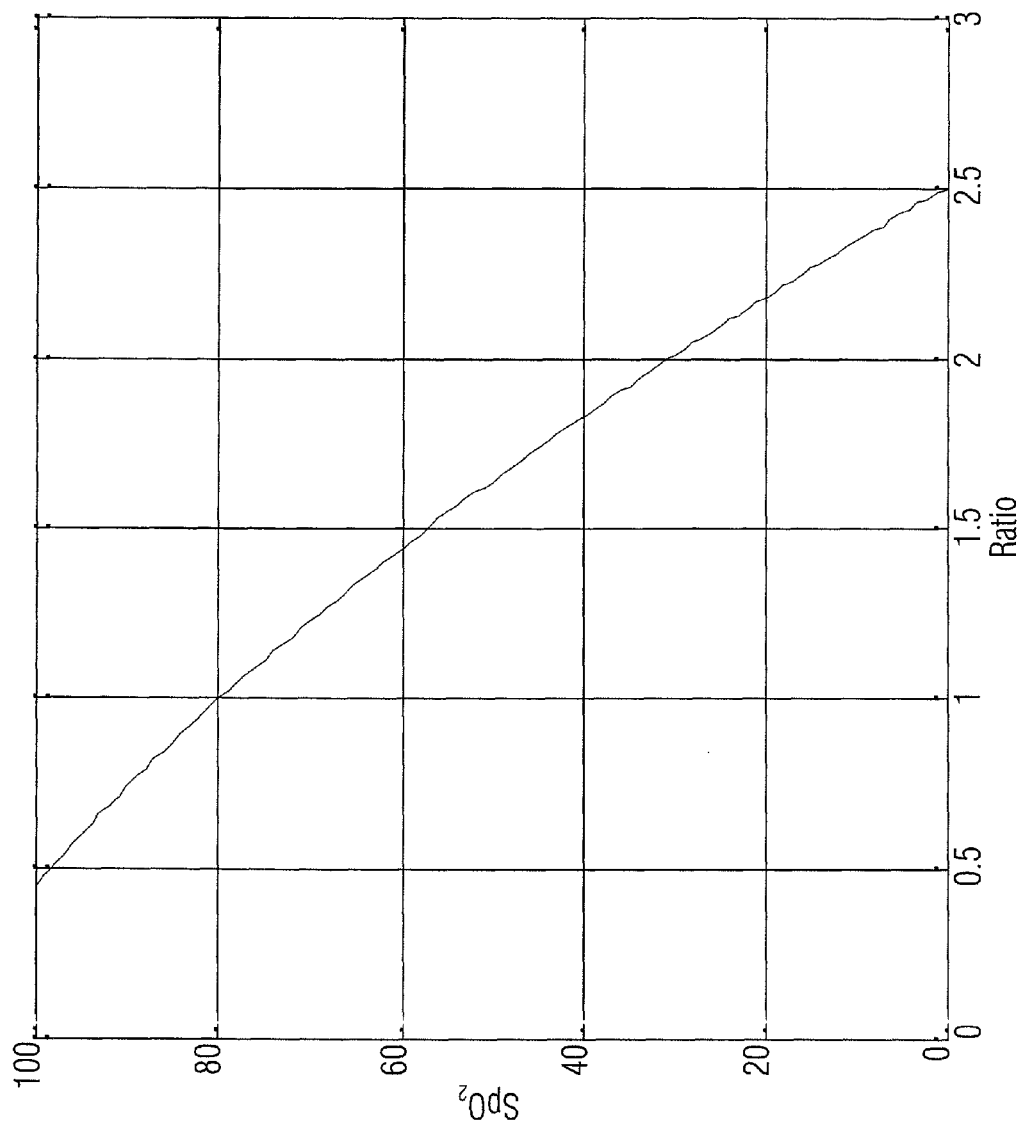
FIG. 23 depicts an exemplary characteristic curve of a calibration function
Figure 24:
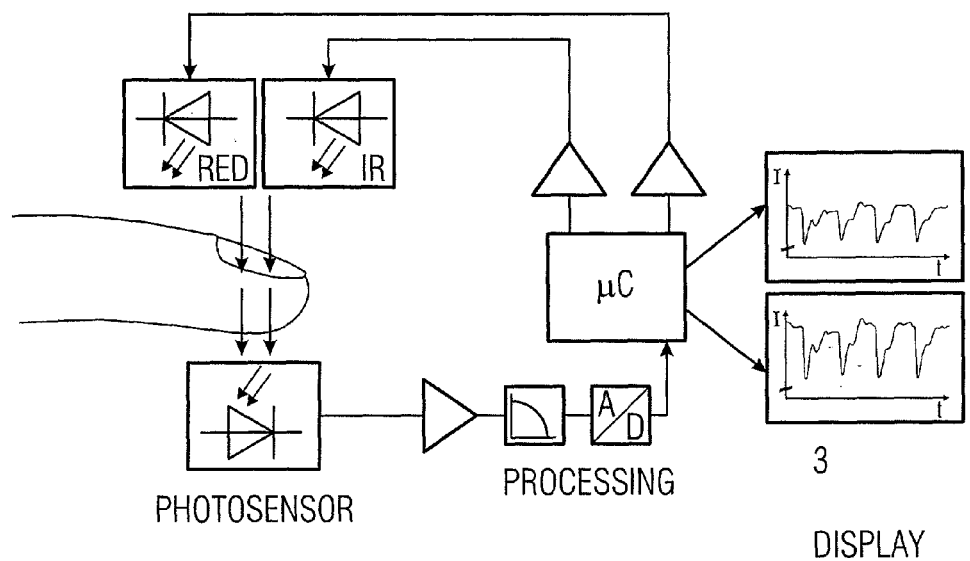
FIG. 24 shows a basic block diagram of the hardware of a conventional pulse oximeter.
Figure 25:
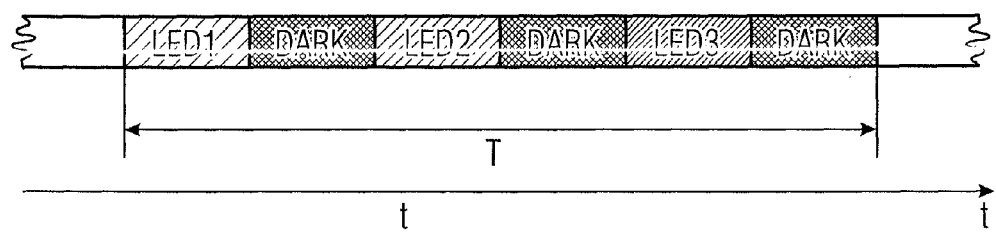
FIG. 25 is a schematized representation of a time division multiple access method (TDMA).

After multiplication by the spectral mask, only the relevant frequency components were detected. According to the same principle as was already described, a quotient of the relevant spectra may now be determined again using the complex total least squares fit method and singular value decomposition. In this context, only those frequency components are used which have been determined by means of the spectral mask. Via these interference-corrected spectra, the original straight line and its slope may now be determined. In addition to the slope of the original straight line, it is also possible to extract a measure of the reliability of the slope determined from the matrix decomposition of the over-determined linear equation system. The variance in accordance with the Frobenius norm, which may be directly obtained from the matrix decomposition, indicates the similarity of the two signals. The variance is used as an indictor of excessive interference effects which prevents the computation of the physiological parameters within the specified tolerance range. Then this variance can be output at output 355 in accordance with FIG. 3. The complex total least squares fit method has a calibration function 360 connected downstream from it. The slope of the original straight line which has been determined using the complex total least squares fit method and which is representative of the blood saturation value of the subject is passed on to a calibration function 360. The calibration function directly associates $SpO_2$ values (blood saturations values) with the slope values obtained. The respective $SpO_2$ values are then output, in accordance with FIG. 3, at output 365. FIG. 23 shows an exemplary characteristic curve of a calibration function. It can be seen how blood saturation values ($SpO_2$ values) are associated with quotients (ratio). The characteristic curves of the calibration function are empirically determined using reference measurements.

One advantage of the present invention is that spread spectrum modulation, which is specifically tailored to the field of application of plethysmography and pulse oximetry, and the combination of the specifically adapted adaptive filtering significantly improve the reliability of the plethysmograms and enable effective filtering of ambient-light interferences and interferences caused by electromagnetic fields (e.g. high-frequency surgery).

Another advantage is that using singular value decomposition for calculating $SpO_2$ values from the complex spectra, a measure of reliability in the form of a variance may be extracted and used for assessing the quality of the result, or that a malfunction may be reliably detected.

An additional advantage is that using the inventive apparatus for measuring the blood oxygen saturation and heart rate, reliable measurements may be made even at a low arterial blood volume pulsation while the patient is moving.

In general terms, one may state that the quality of treatment for a patient, in particular in intensive care and in operating rooms, may be considerably improved by the present invention. Due to the increased reliability and robustness of the method, diagnostic errors due to distorted measurements and/or due to unreliable measurement values can be considerably reduced.

While this invention has been described in terms of several embodiments, there are alterations, permutations, and equivalents which fall within the scope of this invention.

It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for determining a physiological parameter of a living being, comprising:
   a receiver adapted to receive iterating optical signals, an optical signal comprising sequences, and a sequence comprising at least two bright periods during which a transmit light source adopts an on state and at least two dark periods during which no transmit light source adopts an on state, and the at least two bright periods being irregularly arranged within a sequence, and
   an extractor for extracting information on the physiological parameter from the receive signal, the extractor being adapted either to receive, to store or to generate binary code words comprising a length and indicating an arrangement of the bright and dark periods, and to link a binary code word with the signals in a block-by-block manner so as to obtain a digital signal of a bright transmit channel, the bright transmit channel being determined by the binary code word, and to link two other binary code words with the signals so as to obtain two digital signals of two dark transmit channels which are determined by the two other binary code words, and the extractor being adapted to extract, on the basis of the digital signal of the bright transmit channel and of the two digital signals of the dark transmit channels, a value of a magnitude indicating the physiological parameter, the extractor being implemented to form a differential signal from the two dark transmit channels, and to reduce an aliasing interference in the digital signal of the bright transmit channel by means of a spectral analysis of the differential signal.

2. The apparatus as claimed in claim 1, wherein the sequence of the optical signal is based on a clock in accordance with which the bright and dark periods occur, and the extractor comprises:
a clock circuit implemented to receive the clock from a controller, to extract the clock from the receive signal, or to generate the clock by itself using a clock generator; and
an analog/digital converter implemented to receive the clock signal from the clock circuit and to convert the receive signal to a digital receive signal in dependence on the clock.

3. The apparatus as claimed in claim 2, wherein the extractor is implemented to operate at a clock higher than 800 Hz.

4. The apparatus as claimed in claim 1, wherein the extractor is implemented to form a scalar product between the binary code word and a block of digital receive signal values of a length of the binary code word, to weight the result, to link it with other results and to associate an overall result with a transmit channel.

5. The apparatus as claimed in claim 1, wherein the extractor is implemented to subtract a values of a dark transmit channel from those of the bright transmit channel.

6. The apparatus as claimed in claim 1, wherein the sequence of the optical signal comprises at least two further bright periods originating from a second transmit light source, the extractor being implemented to extract a further bright transmit channel using a further binary code word.

7. The apparatus as claimed in claim 1, wherein the extractor is implemented to determine a value for interferences from the dark transmit channels, and to improve the signal quality of the bright transmit channels by combining the value with a values of the bright transmit channels.

8. The apparatus as claimed in claim 1, wherein the extractor comprises an adaptive filter and wherein, in addition, the extractor is implemented to set the adaptive filter such that, at a frequency of the aliasing interference, it allows less signal power to pass than at frequencies which do not belong to the aliasing interference.

9. The apparatus as claimed in claim 1, wherein the extractor is implemented to form columns of a matrix from the differential signal of two dark channels in a block-by-block manner, to regard these as coefficients of a linear over-determined equation system, and to solve by an optimization criterion, as well as to adaptively track the coefficients.

10. The apparatus as claimed in claim 1, wherein the extractor is implemented to multiply signals of transmit channels which are subdivided into blocks by a window function, to normalize them and/or to determine their spectra.

11. The apparatus as claimed in claim 1, wherein the extractor is implemented to determine a straight regression line in a large group of dots using a CTLSF method (complex total least squares fit) by means of a singular value decomposition.

12. The apparatus as claimed in claim 1, wherein the extractor is implemented to determine the linear coefficient using the CTLSF method (complex total least squares fit) for two linearly dependent spectra comprising independent interferences.

13. The apparatus as claimed in claim 12, wherein the extractor is implemented to determine the linear coefficient using a singular value decomposition.

14. The apparatus as claimed in claim 1, wherein the extractor is implemented to determine, from a ratio of two spectral values of the two bright transmit channels, blood oxygen saturation in a form of an $SpO_2$ value of an artery which has been radiated.

15. The apparatus as claimed in claim 1, wherein the extractor is implemented to determine heart rate frequency signals using a spectral analysis of the bright transmit channels.

16. The apparatus as claimed in claim 15, wherein the extractor is implemented to determine a spectral mask which insulates, in the frequency range, those signal portions from a spectrum which comprise the same spectral characteristic as a signal sought for.

17. The apparatus as claimed in claim 16, wherein the extractor is implemented to determine a spectral mask for pulse signals with regard to a potential fundamental wave frequency and potential harmonic frequencies, as well as their relation to each other, from a spectra of the bright transmit channels.

18. The apparatus as claimed in claim 17, wherein the extractor is implemented to infer a subject's heart rate from a relation of fundamental wave components and harmonic components within the spectrum of the bright transmit channels.

19. The apparatus as claimed in claim 15, wherein the extractor is implemented to utilize, for spectral analysis, only such frequency portions of the spectrum which are relevant to the pulse portion.

20. The apparatus as claimed in claim 1, wherein the extractor is implemented to receive, to store or to generate a table which associates blood saturation values ($SpO_2$) with quotients of spectral values.

21. The apparatus as claimed in claim 1, wherein the extractor is implemented to output a reliability measure of the physiological parameter determined.

22. The apparatus as claimed in claim 21, wherein the extractor is implemented to determine the reliability measure from a singular values of a matrix composed of two spectra of two bright transmit channels, a spectrum of the bright transmit channel representing a column of the matrix.

23. The apparatus as claimed in claim 22, wherein the extractor is adapted to derive the reliability measure from the Frobenius norm of the matrix.

24. The apparatus as claimed in claim 21, wherein the extractor is implemented to determine a variance of the difference between two bright transmit channels and to derive the reliability measure therefrom.

25. The apparatus as claimed in claim 21, wherein the extractor is implemented to determine a variance from the difference between bright transmit channels comprising reduced interference, and to derive the reliability measure therefrom.

26. A method of determining a physiological parameter of a living being, comprising:
receiving iterating optical signals, an optical signal comprising sequences, and a sequence comprising at least two bright periods during which a transmit light source adopts an on state and at least two dark periods during which no transmit light source adopts an on state, and the at least two bright periods being irregularly arranged within a sequence, and
extracting information on the physiological parameter from the receive signal, binary code words which comprise a length and indicate an arrangement of the bright and dark periods being either received, stored or generated;

linking a binary code word with the signals in a block-by-block manner so as to obtain a digital signal of a bright transmit channel, the bright transmit channel being determined by the binary code word;

linking two other binary code words with the signals so as to obtain two digital signals of two dark transmit channels which are determined by the two other binary code words;

extracting, on the basis of the digital signal of the bright transmit channel and of the two digital signals of the dark transmit channels, a value of a magnitude indicating the physiological parameter, the extracting comprising forming a differential signal from the two dark channels, and an aliasing interference in the digital signal of the bright transmit channel being reduced by means of a spectral analysis of the differential signal.

* * * * *

UNITED STATES PATENT AND TRADEMARK OFFICE
CERTIFICATE OF CORRECTION

PATENT NO.       : 8,398,557 B2                                                Page 1 of 1
APPLICATION NO.  : 12/280156
DATED            : March 19, 2013
INVENTOR(S)      : Tobola et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1185 days.

Signed and Sealed this

First Day of September, 2015

Michelle K. Lee
*Director of the United States Patent and Trademark Office*